(12) United States Patent
Charlas et al.

(10) Patent No.: US 10,414,867 B2
(45) Date of Patent: Sep. 17, 2019

(54) FLUOROETHER UNIT-BASED THERMOSTABLE, LOW-$T_g$ AND THERMOSETTING CROSS-LINKED MATERIALS

(71) Applicants: SAFRAN ELECTRICAL & POWER, Blagnac (FR); UNIVERSITE DE MONTPELLIER, Montpellier (FR); CENTRE NATIONAL DE LA RECHERCHE SCIENTIFIQUE (CNRS), Paris (FR)

(72) Inventors: Mathieu Charlas, Blagnac (FR); Donatien Henri Edouard Martineau, Blagnac (FR); Gerald Pierre Maurice Lopez, Lunel-Viel (FR); Jean-Pierre Habas, Montpellier (FR); Bruno Ameduri, Montpellier (FR)

(73) Assignees: SAFRAN ELECTRICAL & POWER, Blagnac (FR); UNIVERSITE DE MONTPELLIER, Montpellier (FR); Centre National De La Recherche Scientifique (CNRS), Paris (FR)

( * ) Notice: Subject to any disclaimer, the term of this patent is extended or adjusted under 35 U.S.C. 154(b) by 0 days.

(21) Appl. No.: 15/741,048

(22) PCT Filed: Jul. 1, 2016

(86) PCT No.: PCT/FR2016/051676
§ 371 (c)(1),
(2) Date: Dec. 29, 2017

(87) PCT Pub. No.: WO2017/001806
PCT Pub. Date: Jan. 5, 2017

(65) Prior Publication Data
US 2018/0186934 A1 Jul. 5, 2018

(30) Foreign Application Priority Data

Jul. 1, 2015 (FR) ..................... 15 56208

(51) Int. Cl.
*C08K 5/00* (2006.01)
*C08K 5/28* (2006.01)
(Continued)

(52) U.S. Cl.
CPC ............. *C08G 73/08* (2013.01); *C07C 41/30* (2013.01); *C07C 247/04* (2013.01);
(Continued)

(58) Field of Classification Search
CPC  C08L 63/00; C08L 71/12; C08K 5/10; C08K 5/17; C08K 5/3472
See application file for complete search history.

(56) References Cited

U.S. PATENT DOCUMENTS

2008/0311412 A1* 12/2008 Fokin ................ C08G 73/0605
428/457
2010/0324234 A1  12/2010 Hung et al.
(Continued)

FOREIGN PATENT DOCUMENTS

WO  WO 2010/115855 A1  10/2010
WO  WO 2012/131278 A1  10/2012
WO  WO 2014/055406 A2  4/2014

OTHER PUBLICATIONS

International Search Report dated Oct. 7, 2016 in PCT/FR2016/051676 (with English translation), 6 pages.
(Continued)

*Primary Examiner* — Shane Fang
(74) *Attorney, Agent, or Firm* — Oblon, McClelland, Maier & Neustadt, L.L.P.

(57) ABSTRACT

The present invention relates to a cross-linkable composition comprising: i) a fluorinated α,ω-bis(propargyl) oligomer of
(Continued)

formula (I): in which m is 1 to 100, e.g. 1 to 93, n is 2 to 150, e.g. 1 to 128, p is 0 to 2, preferably 0 or 1.75, and n, m and p are selected such that the fluorinated α,ω-bis(propargyl) oligomer of formula (I) has a number average molar mass $M_n$ of 400 to 25000; ii) a cross-linking agent comprising at least three azide-$N_3$ groups; and iii) optionally, a fluorinated oligomer comprising two terminal azide-N3 or fluorinated α,ω-bis(azide) oligomer groups. The invention also relates to a material comprising the click chemistry reaction product of the cross-linkable composition of the invention, to a method for preparing said material and to the uses thereof.

14 Claims, 24 Drawing Sheets

(51) Int. Cl.
C07C 41/30 (2006.01)
C08G 65/00 (2006.01)
C08G 73/08 (2006.01)
C08L 71/00 (2006.01)
C07C 247/04 (2006.01)
C08G 65/333 (2006.01)
C08G 65/337 (2006.01)

(52) U.S. Cl.
CPC ......... *C08G 65/007* (2013.01); *C08G 65/333* (2013.01); *C08G 65/337* (2013.01); *C08G 65/33365* (2013.01); *C08K 5/0025* (2013.01); *C08K 5/28* (2013.01); *C08L 71/00* (2013.01); *C08G 2650/20* (2013.01); *C08G 2650/60* (2013.01)

(56) References Cited

U.S. PATENT DOCUMENTS

2012/0028858 A1 2/2012 Wadgaonkar et al.
2015/0259450 A1 9/2015 Corveleyn et al.

OTHER PUBLICATIONS

Ying-Wei Yang, et al., ""Clicked" Fluoropolymer Elastomers as Robust Materials for Potential Microfluidic Device Applications", Journal of Materials Chemistry, vol. 22 No. 3, XP055267631, Nov. 17, 2012, pp. 1100-1106.

Gérald Lopez, et al., "A Versatile Strategy to Synthesize Perfluoropolyether-Based Thermoplastic Fluropolymers by Alkyne-Azide Step-Growth Polymerization", Macromolecular Rapid Communications, vol. 37 No. 8, XP055308095, Feb. 23 2016, pp. 711-717.

T.E. Karis, et al., "Perfluoropolyether Characterization by Nuclear Magnetic Resonance Spectrosopy and Gel Permeation Chromatography", Journal of Fluorine Chemistry, Dec. 2002, pp. 1-14 with cover page.

Mohamed Touaibia, et al., "Tri- and Hexavalent Mannoside Clusters as Potential Inhibitors of Type 1 Fimbriated Bacteria using Pentaerythritol and Triazole Linkages", Chemical Communications, 2007, pp. 380-382, with cover page.

Georgi Kostov, et al., "Synthesis and Characterizations of Photo-Cross-Linkable Telechelic Diacrylate Poly(vinylidene fluoride-co-perfluoromethyl Vinyl Ether Copolymers", Macromolecules, vol. 45, 2012, pp. 7375-7387.

Ghislain David, et al., "Use of Iodocompounds in Radical Polymerization", Chemical Reviews, vol. 106 No. 9, 2006, pp. 3936-3962.

Cyrille Boyer, et al., "Telechelic Diiodopoly(VDF-co-PMVE) Copolymers by Iodine Transfer Copolymerization of Vinylidene Fluoride (VDF) with Perfluoromethyl Vinyl Ether (PMVE)", Macromolecules, vol. 43 No. 8, 2010, pp. 3652-3663.

Kim Clegg, et al., "Chelation-controlled Molecular Morphology: a minal to imine rearrangements", Dalton Transactions, vol. 41 No. 15, Apr. 21, 2012, pp. 4335-4357 with cover page.

Xiaomin Qian, et al., "Star-branched amphiphilic PLA-b-PDMAEMA copolymers for co-delivery of miR-21 inhibitor and doxorubicin to treat glioma", Biomaterials, vol. 35, 2014, pp. 2322-2335.

* cited by examiner

FLUOROETHER UNIT-BASED THERMOSTABLE, LOW-$T_g$ AND THERMOSETTING CROSS-LINKED MATERIALS

FIELD OF THE INVENTION

The present invention concerns the field of fluoropolyether-based thermosetting materials and/or elastomers, processes for preparing same and uses thereof.

STATE OF THE ART

Many applications falling with the field of electrical or electronic engineering require materials having very high mechanical flexibility over a wide range of temperatures in harsh chemical environments. These same materials find use as encapsulants or moldings in microelectronic assemblies for the transport sector. They must have good electrical insulation properties and preferably a controlled density (typically a density of 3 or lower).

The most concrete example describing the interest in encapsulation is that presented by the rapidly-growing field of power-module technology, notably in the aviation industry, in particular through research programs aiming to define a "more electric" aircraft, but also in the automobile industry, notably for vehicles with electric, hybrid or fuel-cell engines. However, the materials currently used for these applications (silicone, polyurethane, epoxy, etc.) are not sufficiently resistant at high temperature (typically above 250° C., indeed above 300° C.), notably in harsh environments (saturated humidity, hydrocarbon vapor or phosphate ester vapor).

A solution proposed in the prior art consists in substituting silicone-, polyurethane- or epoxy-type materials with fluoropolyether-based materials having a low glass-transition temperature ($T_g$).

Particular mention may be made of patent application WO 2014/055406, which calls upon the reaction of a first compound (co-agent) functionalized with three azide (—$N_3$) groups, and a second bis-propargyl or bis-nitrile type compound, and optionally a third compound functionalized with at least two azide (—$N_3$) groups synthesized from a polyisocyanate by reaction with 2-azidoethanol. Said reaction is described as cross-linking because it leads to the production of a three-dimensional polymer network. The only bis-propargyl compound exemplified contains terminal —C(=O)NH—$CH_2$—C≡CH groups, i.e., comprising a mono-propargylamide group, which has low chemical resistance, particularly under humid conditions. Thus, the introduction of these amide moieties into the structure of the terminal polymers precludes any use under harsh humid conditions, notably at a temperature above 250° C.

Yang et al. (*Journal of Materials Chemistry*, Vol. 22, No. 3, November 2011) disclose elastomers obtained by a click-chemistry reaction between a fluorinated α,ω-bis(propargyl) oligomer of formula (I):

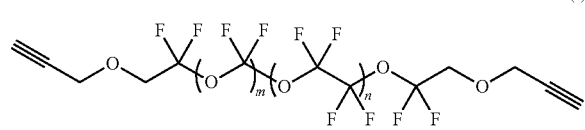

(I)

and the following cross-linking agent:

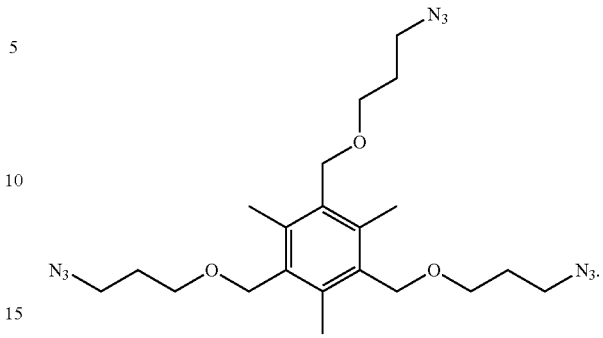

However, these materials have a glass-transition temperature of −10° C.

Document WO 2010/115855 does not disclose a particular general structure for the alkyne compound used (see in particular paragraphs [0032] and [0033]). Furthermore, it appears upon reading paragraphs [0037]-[0041] (definition of substituent $R_H$) that the alkyne used is a mono-alkyne and not a diyne. This point is confirmed by Examples 1 and 2 (step 3), wherein only the phenylacetylene is used.

In document US 2010/324234, the diyne used is either a fluoroether comprising two acetylene groups (see paragraph [0014]), or an aromatic fluoroether. In both cases, the diyne is different from that used in the present invention.

There thus exists a need for materials combining the properties of electrical insulation, mechanical flexibility over a broad temperature range, typically ranging from −100° C. to +300° C., having in particular at least one glass-transition temperature value of −70° C. or lower, and increased chemical resistance, in particular in harsh and/or humid environments.

SUMMARY OF THE INVENTION

The Applicant solved this technical problem by means of materials comprising the product of the click-chemistry reaction between:
i) a fluorinated α,ω-bis(propargyl) oligomer comprising a fluoroether chain free of amide groups;
ii) a cross-linking agent comprising at least three azide (—$N_3$) groups (preferably easily synthesizable); and
iii) optionally a fluorinated oligomer comprising two terminal azide (—$N_3$) groups (also called fluorinated α,ω-bis(azide) oligomer).

The materials according to the invention are thus cross-linked materials, resulting from the polymerization of bifunctional oligomers in the presence of a cross-linking agent.

The flexibility (elastic nature) and the glass-transition temperature of the polymers according to the invention can be modulated as desired as a function of two parameters:
the relative proportion of cross-linking agent and of fluorinated α,ω-bis(azide) oligomer, and
the nature and length of the fluorinated chain of the fluorinated α,ω-bis(propargyl) (i) and optionally α,ω-bis(azide) (iii) oligomers.

In other words, as a function of these two parameters, the polymers according to the invention will fall within the category of thermosetting polymers, or that of elastomers. Thus, the polymers according to the invention can have a glass-transition temperature of the order of −100° C., particularly −150° C. to −30° C. Furthermore, as a function of the above-mentioned parameters the polymers according to the invention are either amorphous or crystalline.

This dual versatility permits the development of a range of polymers capable of meeting a variety of specifications while limiting development costs.

Advantageously, the proportions of the various reagents are such that the total number of azide groups provided either by the fluorinated chain of the α,ω-bis(azide) oligomer or by the cross-linking agent is equal to the number of propargyl groups provided by the fluorinated α,ω-bis(propargyl) oligomer.

Furthermore, independently of these features, the polymers according to the invention exhibit a good chemical inertia on account of the presence of fluorinated groups and the absence of amide groups in the polymer chain.

Thus, an aspect of the present invention concerns a cross-linkable composition comprising:

i) a fluorinated α,ω-bis(propargyl) oligomer of formula (I):

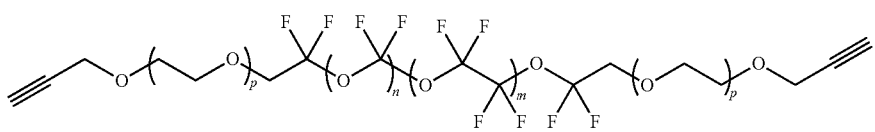

wherein m is 1 to 100, for example 1 to 93,
n is 2 to 150, for example 1 to 128, and
p is 0 to 2, for example 0 or 1.75,
n, m and p being selected such that the fluorinated α,ω-bis(propargyl) oligomer of formula (I) has a number-average molar mass ($M_n$) of 400 to 25000;

ii) a cross-linking agent comprising three azide (—$N_3$) groups; and iii) optionally, a fluorinated oligomer comprising two terminal azide (—$N_3$) groups (also called fluorinated α,ω-bis(azide) oligomer).

Another aspect of the invention is directed to a material comprising the product of the click-chemistry reaction between:

i) a fluorinated α,ω-bis(propargyl) oligomer of formula (I):

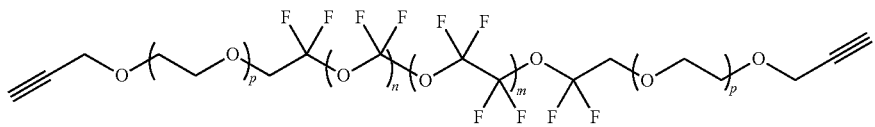

wherein m is 1 to 100, for example 1 to 93,
n is 2 to 150, for example 1 to 128, and
p is 0 to 2, for example 0 or 1.75,
n, m and p being selected such that the fluorinated α,ω-bis(propargyl) oligomer of formula (I) has a number-average molar mass ($M_n$) of 400 to 25000;

ii) a cross-linking agent comprising at least three azide (—$N_3$) groups; and iii) optionally, a fluorinated oligomer comprising two terminal azide (—$N_3$) groups (also called fluorinated α,ω-bis(azide) oligomer).

Another aspect of the invention concerns a process for preparing the material according to the invention.

Another aspect of the invention concerns the use of the material according to the invention as electrical insulator.

Definitions

Unless otherwise specified, in the present description, the indices m, n, p, q, r, s and i are positive real numbers which are not necessarily whole but representative of the average molecular structure (statistical values).

The term "materials," within the meaning of the present invention, refers to a cross-linked material resulting from the polymerization of bifunctional oligomers in the presence of a cross-linking agent. In other words, the material according to the invention comprises or consists of the product of the click-chemistry reaction of the cross-linkable composition according to the invention. The materials according to the present invention are comparable to thermosetting materials or to elastomers, notably as a function of the mesh density of their three-dimensional network.

The term "click-chemistry reaction," within the meaning of the present invention, refers to a 1,3-dipolar cycloaddition reaction (or Huisgen reaction) between a compound comprising an azide group and a compound, comprising an alkyne group, preferably in the presence of a copper or ruthenium catalyst, to provide a 1,2,3-triazole group according to the following reaction pathway:

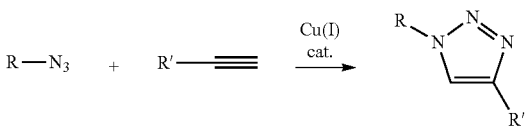

-continued

When a copper catalyst (copper(I) salt or copper(II) salt) is used, the click-chemistry reaction leads predominantly (even exclusively, as a function of the substrates) to a 1,4-disubstituted 1,2,3-triazole.

When a ruthenium catalyst is used, the click-chemistry reaction leads predominantly (even exclusively, as a function of the substrates) to a 1,5-disubstituted 1,2,3-triazole.

The term "thermosetting polymer," within the meaning of the present invention, refers to a polymer which can be used only once and which becomes infusible and insoluble after polymerization of a single- or multi-component composition that is generally liquid in the initial state. Said polymerization also includes a "cross-linking," based on the production of a three-dimensional polymer network. Once cured, the polymer cannot revert to the liquid state.

The term "elastomer," within the meaning of the present invention, refers to a polymer with "elastic" properties, obtained after cross-linking. It tolerates very large deformations before breaking. The term "rubber" is a common synonym for elastomer.

The "glass-transition temperature" or "$T_g$" is a parameter well-known to persons skilled in the art. It is the critical temperature above which the material passes from a rubbery state to a glassy, solid (rigid) state (and vice versa). It can be measured by differential scanning calorimetry (DSC), preferentially through a high temperature ramp advantageously greater than 5° C./min. Other techniques known to persons skilled in the art make it possible to record a physical property discontinuity when passing the glass transition. For example, mention may be made of dynamic rheometry, measurements of dielectric spectroscopy or dilatometry.

The decomposition temperature associated with a 10% weight loss value ($T_d^{10\%}$) is also a parameter well-known to persons skilled in the art, making it possible to measure the thermal stability of a polymer. In particular, it is measured by thermogravimetric analysis, notably under oxidizing conditions (in air) or in inert environment (nitrogen gas). The choice of analysis atmosphere is influenced by the wish to discriminate purely thermal degradation phenomena (nitrogen gas atmosphere) from those concerning thermo-oxidative processes (air atmosphere).

According to the present invention, the number-average molar mass ($M_n$) is measured by $^{19}F$ NMR spectroscopy. Thus, the number-average molar mass is preferably measured according to the method described in Karis et al. (*J. Fluorine Chem.* 2002, 118, 81-94). An exemplary implementation of this method is notably described in FIG. 1: the number m is calculated as being equal to the ratio of 2 times the integration of the O—$CF_2$—O peak to the integration of the $CF_2CH_2OH$ peak, whereas the number n is calculated as being equal to the ratio of 2 times the integration of the O—$CF_2CF_2$—O peak to the integration of the $CF_2CH_2OH$ peak, with integration meaning the area measured under the corresponding peak in the $^{19}F$ NMR spectrum. The determination of n and m then makes it possible to calculate the number-average molar mass ($M_n$).

The term "amide group," within the meaning of the present invention, refers to an —R—C(=O)—NH— group or an —NH—C(=O)—R—(C=O)NH—R' group, with R and R' being independently selected for example from an alkyl group, an aryl or heteroaryl group, or a mixed fluorine-carbon chain.

The term "harsh environment," within the meaning of the present invention, refers to an environment exposed to (or saturated with) hydrocarbon vapor or phosphate ester vapor, at a temperature typically of 200° C. to 350° C., particularly 250° C. to 350° C. A "harsh environment" may also be an environment having a relative humidity of 50% to 100%, at a temperature, of 120° C. or lower at normal atmospheric pressure (1 bar) or higher (preferably nevertheless of 20 bar or lower).

The term "$C_1$-$C_6$ alkyl," within the meaning of the present invention, refers to a linear or branched, saturated 6-carbon hydrocarbon chain. By way of example of a $C_1$-$C_6$ alkyl, particular mention may be made of methyl, ethyl, propyl, n-butyl, s-butyl, tert-butyl, pentyl, isopentyl, n-hexyl. Within the meaning of the present invention, a $C_1$-$C_6$ alkyl also includes $C_3$-$C_6$ cyclic alkyls, such as cyclopropyl, cyclobutyl, cyclopentyl and cyclohexyl. Preferably, the $C_1$-$C_6$ alkyl is a $C_1$-$C_4$ alkyl. Methyl and ethyl are particularly preferred.

The term "$C_2$-$C_6$ alkenyl," within the meaning of the present invention, refers to a linear or branched 6-carbon hydrocarbon chain comprising at least one unsaturation (C=C double bond), which is not aromatic. By way of example of a $C_2$-$C_6$ alkenyl, particular mention may be made of ethylenyl (or vinyl), 1-propenyl, ally) (2-propenyl), n-butenyl. Preferably, the $C_2$-$C_6$ alkenyl is a $C_2$-$C_4$ alkenyl. Vinyl is particularly preferred.

Within the meaning of the present invention, the term "aliphatic" refers to both alkyls and alkenyls.

Within the meaning of the present invention, an aromatic group is an aryl or a heteroaryl.

The term "aryl," within the meaning of the present invention, refers to an aromatic hydrocarbon group preferably comprising 6 to 10 carbon atoms, and comprising one or more fused rings, such as for example a phenyl, indanyl or naphthyl group. Advantageously, it is phenyl.

The term "heteroaryl" or "heteroaromatic," within the meaning of the present invention, refers to an aromatic group comprising 5 to 10 cyclic atoms including one or more heteroatoms, advantageously 1 to 4 and even more advantageously 1 or 2, such as for example sulfur, nitrogen or oxygen atoms, the other cyclic atoms being carbon atoms. Examples of heteroaryl groups include furyl, thienyl, pyrrolyl, pyridinyl, pyrimidinyl, pyrazolyl, imidazolyl, triazolyl, tetrazolyl or indyl groups.

The term "propargyl compound," within the meaning of the present invention, refers to a compound comprising the chemical group of formula —$CH_2$—C≡CH (propargyl radical).

The term "α,ω-bis(propargyl) oligomer," within the meaning of the present invention, refers to an oligomer comprising two terminal propargyl (—$CH_2$—C≡CH) groups. The α,ω-bis(propargyl) oligomer according to the invention does not comprise any amide group.

The term "cross-linking agent comprising at least three azide (—$N_3$) groups," within the meaning of the present invention, refers to a molecule comprising at least three azide (—$N_3$) groups and having a molecular mass of 200 to 1000 g/mol. The cross-linking agent according to the invention does not comprise any amide group.

The term "pentaerythritol triazide" refers to the compound of formula:

The term "α,ω-bis(azide) oligomer," within the meaning of the present invention, refers to an oligomer comprising two terminal azide (—$N_3$) groups. The α,ω-bis(azide) oligomer according to the invention does not comprise any amide group.

The term "leaving group," within the meaning of the present invention, refers to a chemical group that can be easily displaced by a nucleophile during a nucleophilic substitution reaction, the nucleophile being more particularly an azide (—N$_3$) group. Such a leaving group may be more particularly a halogen atom such as a chlorine, bromine or iodine atom, or a sulfonate group such as a mesylate (—OS(O$_2$)—CH$_3$), a triflate (—OS(O)$_2$—CF$_3$) or a tosylate (—OS(O)$_2$-(p-Me-C$_6$H$_4$)).

DETAILED DESCRIPTION OF THE INVENTION

Cross-Linkable Compositions

The present invention concerns, firstly, a cross-linkable composition comprising:

i) a fluorinated α,ω-bis(propargyl) oligomer of formula (I):

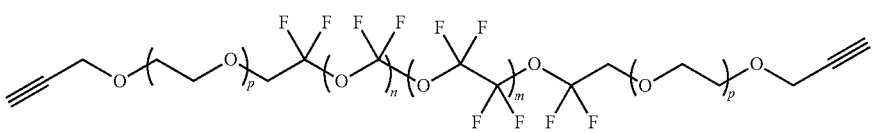

wherein m is 1 to 100, for example 1 to 93,
n is 2 to 150, for example 1 to 128, and
p is 0 to 2, for example 0 or 1.75,
n, m and p being selected such that the fluorinated α,ω-bis(propargyl) oligomer of formula (I) has a number-average molar mass (M$_n$) of 400 to 25000;

ii) a cross-linking agent comprising at least three azide (—N$_3$) groups; and iii) optionally, a fluorinated oligomer comprising two terminal azide (—N$_3$) groups (also called fluorinated α,ω-bis(azide) oligomer).

Advantageously, the cross-linkable compositions according to the invention comprise a total number of propargyl (—CH$_2$—C≡CH) groups equal to the total number of azide (—N$_3$) groups. In other words, the respective molar proportions of oligomers (ii) and (iii) are such that the total number of propargyl (—CH$_2$—C≡CH) groups is equal to the total number of azide (—N$_3$) groups.

For example, the relative proportions of cross-linking agent comprising three azide (—N$_3$) groups (ii) and of fluorinated α,ω-bis(azide) oligomer (iii) are such that 20 mol % of the azide (—N$_3$) groups are provided by the cross-linking agent comprising three azide (—N$_3$) groups, relative to the total number of azide groups in the cross-linkable composition according to the invention.

In a second example, the relative proportions of cross-linking agent comprising three azide (—N$_3$) groups (ii) and of fluorinated α,ω-bis(azide) oligomer (iii) are such that 40 mol % of the azide (—N$_3$) groups are provided by the cross-linking agent comprising three azide (—N$_3$) groups, relative to the total number of azide groups in the cross-linkable composition according to the invention.

In a third example, the relative proportions of cross-linking agent comprising three azide (—N$_3$) groups (ii) and of fluorinated α,ω-bis(azide) oligomer (iii) are such that 60 mol % of the azide (—N$_3$) groups are provided by the cross-linking agent comprising three azide (—N$_3$) groups, relative to the total number of azide groups in the cross-linkable composition according to the invention.

In a fourth example, the relative proportions of cross-linking agent comprising three azide (—N$_3$) groups (ii) and of fluorinated α,ω-bis(azide) oligomer (iii) are such that 80 mol % of the azide (—N$_3$) groups are provided by the cross-linking agent comprising three azide (—N$_3$) groups, relative to the total number of azide groups in the cross-linkable composition according, to the invention.

(i) Fluorinated α,ω-bis(propargyl) Oligomer

The fluorinated α,ω-bis(propargyl) oligomer of formula (I) is particularly advantageous notably because it is free of any amide groups, which are known to be sensitive to humidity. Furthermore, the perfluoropolyether moiety gives it the chemical stability necessary for extended use in harsh environments. Finally, the presence of oxygen atoms in the carbon backbone gives the material obtained after cross-linking by click chemistry an advantageous flexibility for the applications envisaged (encapsulants, joints, etc.), and in any event which is superior to that of a chain comprising only fluorine and carbon atoms.

Preferably, the fluorinated α,ω-bis(propargyl) oligomer of formula (I) has a number-average molar mass (M$_n$) of 400 to 25000 g/mol, more preferably 800 to 4000 g/mol, most preferably 1000 to 2000 g/mol. For example, the fluorinated α,ω-bis(propargyl) oligomer of formula (I) has a number-average molar mass (M$_n$) of about 1250 to 1900 g/mol, notably 1250 to 1300 g/mol or 1750 to 1850 g/mol.

Thus, advantageously, m is 1 to 93 and n is 2 to 128.

In a particular embodiment, p is 1.75. In this case, m typically ranges from 5 to 7 (notably from 5.5 to 6.5), and n typically ranges from 7 to 10 (notably from 8 to 9).

The fluorinated α,ω-bis(propargyl) oligomer of formula (I) is obtained by nucleophilic substitution reaction (S$_N$2) between:

the dial of formula (II):

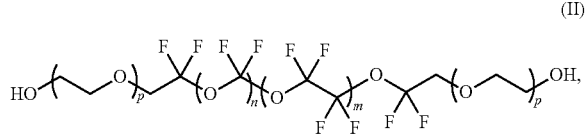

wherein m, n and p are as defined above, and a propargyl compound of formula LG-CH$_2$—C≡CH, wherein LG is a leaving group, for example selected from a sulfonate (RSO$_2$O—) group and a halogen, in particular a mesylate, a triflate, a tosylate, or a chlorine, bromine or iodine atom. Preferably, the propargyl compound is of formula X—CH$_2$—C≡CH, wherein X is a halogen atom, in particular selected from chlorine, bromine and iodine, bromine being preferred. The reaction conditions used for this reaction are conventional for persons skilled in the art, who may be inspired by the article by Yang et al. (*J. Mater. Chem.* 2012, 22, 1100-1106).

For example, if p is 0, the fluorinated α,ω-bis(propargyl) oligomer of formula (I) is obtained by propargylation of the poly(tetrafluoroethylene oxide-co-difluoromethylene oxide)-α,ω-diol sold under the trade name Fomblin® Z-DOL (available notably from Solvay Specialty Polymers), If p is 1.75, it is obtained by propargylation of the poly(tetrafluoroethylene oxide-co-difluoromethylene oxide)-α,ω-diol sold under the trade name Fluorolink® E10H (available notably from Solvay Specialty Polymers).

(ii) Cross-Linking Agent Comprising at Least Three Azide (—$N_3$) Groups (or Triazide)

The cross-linking agent according to the invention does not comprise any amide group.

The cross-linking agent according to the invention contains at least three azide (—$N_3$) groups. Preferably, it contains three azide (—$N_3$) groups.

Furthermore, it is preferable that the three azide (—$N_3$) groups are carried by a molecule of low molar mass which guarantees, by its small size, good molecular mobility and thus high reactivity. At the same time, this dimensional feature gives the reaction mixture leading to the material according to the invention a lower viscosity. Thus, compact triazide cross-linking agents will be preferred.

In particular, the cross-linking agent can be represented by the following formula (III):

$$\text{(III)}$$

[Structure showing central carbon with R_3, R_3, R_3, R_3 groups, and N_3, N_3, N_3, Y substituents]

wherein $R_3$ is a hydrogen atom, a $C_1$-$C_6$ aliphatic group, or an aromatic group, and Y is a group selected from H, OH, an aromatic group, a $C_1$-$C_6$ aliphatic group, an $O(CH_2)_5P(O)(OR_4)_2$ group with
  s an integer from 2 to 20, preferably 2 to 6, more preferably 2,
  $R_4$ being H or a $C_1$-$C_6$ aliphatic group, notably a methyl, ethyl or isopropyl group, preferably methyl.

In a particular embodiment, Y is a group selected from H, OH, a $C_1$-$C_6$ aliphatic group and an aromatic group, preferably OH.

It is known to persons skilled in the art that polymers containing phosphorus atoms have very specific and advantageous properties which enable diverse applications, such as 1. Fire-retardant action (it is known that phosphorous derivatives are excellent fire retardants),
2. Substrate for anti-corrosion and anti-fouling coatings,
3. Adhesion promoter.

Thus, in another embodiment, Y is a $(CH_2)_5P(O)(OR_4)_2$ group with s and $R_4$ as defined above. Preferably, s is then 2 and $R_4$ is preferably $P(O)(OH)_2$ or $P(O)(OCH_3)_2$. In this embodiment, when s is 2, the cross-linking agent is obtained by an oxa-Michael-type reaction between the compound of formula (III) with Y being OH and a compound of formula $CH_2=CH—P(O)(OR_4)_2$ with $R_4$ as defined above. When s is other than 2, the cross-linking agent is obtained by, a radical addition reaction, in the presence of a radical initiator, between a dialkyl hydrogen phosphonate of formula H—$P(O)(OR_4)_2$ with $R_4$ as defined above and a compound of formula (III) wherein Y is an $O(CH_2)_{s-2}CH=CH_2$ group (obtained by reaction between a compound of formula (III) with Y being OH and a compound of formula LG-$(CH_2)_{s-2}CH=CH_2$, with LG being a leaving group for example selected from a sulfonate ($RSO_2O$—) group and a halogen, in particular a mesylate, a triflate, a tosylate, a chlorine, bromine or iodine atom.

Preferably, $R_3$ is a hydrogen atom, a $C_1$-$C_6$ alkyl or a $C_6$-$C_{10}$ aryl group, and/or Y is a group selected from H, OH and a $C_1$-$C_6$ alkyl group or an $O(CH_2)_5P(O)(OR_4)_2$ group with s and $R_4$, as defined above, preferably OH.

More preferably, $R_3$ is a hydrogen atom and Y is OH, $OCH_2CH_2P(O)(OH)_2$ or $OCH_2CH_2P(O)(OCH_3)_2$. In particular, the cross-linking agent can be pentaerythritol triazide.

(iii) Fluorinated α,ω-bis(azide) Oligomer

Preferably, the fluorinated α,ω-bis(azide) oligomer is linear and advantageously of formula (IV):

$$N_3—CHR_1(CHR_2)_q—R_F—(CHR_2)_qCHR_1N_3 \quad \text{(IV)}$$

wherein radical $R_F$ is a fluorinated chain,
q is 0 or 1, and
$R_1$ and $R_2$ are independently selected from a hydrogen atom, a $C_1$-$C_6$ alkyl and a $C_2$-$C_6$ alkenyl.

Preferably, the fluorinated α,ω-bis(azide) oligomer of formula (IV) has a number-average molar mass ($M_n$) of 400 to 25000 g/mol, more preferably 800 to 4000 g/mol, most preferably 1000 to 2000 g/mol.

In a first embodiment, q is 0 and $R_F$ is a fluoropolyether chain.

In particular, in this embodiment the fluorinated α,ω-bis(azide) oligomer is preferably of formula (V):

$$\text{(V)}$$

[Structure of fluorinated oligomer with N_3 end groups, fluorinated chain with F substituents, O linkages, and subscripts p', n', m', p']

wherein m', n' and p' are such as m, n and p above, respectively.

Preferably, the fluorinated α,ω-bis(azide) oligomer of formula (V) has a number-average molar mass ($M_n$) of 400 to 25000 g/mol, more preferably 800 to 4000 g/mol, most preferably 1000 to 2000 g/mol. For example, the fluorinated α,ω-bis(azide) oligomer of formula (V) has a number-average molar mass ($M_n$) of about 1250 to 1900 g/mol, notably 1250 to 1300 g/mol or 1750 to 1850 g/mol.

Thus, advantageously, in this embodiment, m' is 1 to 93, preferably 40 to 93. Preferably, n' is 2 to 128, preferably 50 to 128. Particularly advantageously, m is 40 to 93, and n is 50 to 128. In an embodiment, p' is 0. In another embodiment, p' is 1.75.

The fluorinated α,ω-bis(azide) oligomer of formula (V) is particularly advantageous for the invention notably because it is free of any amide groups. Furthermore, the element fluorine gives it the chemical inertia necessary for extended use in harsh environments. Finally, the presence of oxygen atoms in the polymer chain gives the material obtained after cross-linking by click chemistry an advantageous flexibility for applications requiring particularly plastic cross-linked polymers, notably at high temperatures.

The fluorinated α,ω-bis(azide) oligomer of formula (V) is for example obtained in two steps from the diol of formula (II) above and is presented in patent WO 2010/115855. The first step consists in transforming the two primary hydroxyl groups into leaving groups, for example a sulfonate group, notably selected from mesylate, tosylate and triflate, preferably a tosylate. This first step is typically carried out in the presence of tosyl chloride and a base, such as a trialkylamine, notably triethylamine.

The second step is then nucleophilic substitution in the presence of azide ions, preferably sodium azides. Advantageously, this second step is carried out in a polar aprotic solvent making it possible to solubilize the reagents such as DMSO.

For example, when p' is 0, the fluorinated α,ω-bis(azide) oligomer of formula (V) is obtained according to the following reaction conditions:

1)

HO-[structure]-OH  →  TsCl/Et$_3$N, α,α,α-trifluorotoluene, 55° C., 24 h

TsO-[structure]-OTs

92% yield

2)

TsO-[structure]-OTs  →  NaN$_3$, DMSO, 110° C., 72 h

N$_3$-[structure]-N$_3$

93% yield

In a second embodiment, p is 1, and chain $R_F$ is a perfluorinated chain. Advantageously, $R_1$ is a hydrogen atom and $R_2$ is selected from a hydrogen atom, a methyl or a vinyl, or $R_2$ is a hydrogen atom and $R_1$ is selected from a hydrogen atom, a methyl or a vinyl. Preferably, $R_2$ is a hydrogen atom and $R_1$ is selected from a hydrogen atom, a methyl or a vinyl.

Typically, chain $R_F$ results from the iodine transfer polymerization (ITP) reaction such as detailed for example in *Chem. Rev.* 2006, 106, 3936-3962, and which employs the compound I—C$_4$F$_8$—I and one or more fluorinated olefins, preferably one, two or three fluorinated olefins selected from:
tetrafluoroethylene (TFE, F$_2$C=CF$_2$)
vinylidene fluoride (VDF, H$_2$C=CF$_2$)
hexafluoropropylene (HFP, F$_2$C=CF—CF$_3$)
trifluoroethylene (TrFE, F$_2$C=CHF)
perfluoro(methyl vinyl ether) (PMVE, F$_2$C=CF—OCF$_3$)
3,3,3-trifluoropropene (TFP, H$_2$C=CH—CF$_3$)
2,3,3,3-tetrafluoropropene (R-1234yf, H$_2$C=CF—CF$_3$)
1,3,3,3-tetrafluoropropene (R-1234ze, trans FHC=CH—CF$_3$)
chlorotrifluoroethylene (CTFE, F$_2$C=CFCl)
bromotrifluoroethylene (BTFE, F$_2$C=CFBr)
iodotrifluoroethylene (ITFE, F$_2$C=CFI)
2-chloro-3,3,3-trifluoropropene (1233xf, H$_2$C=CCl—CF$_3$)
vinyl fluoride (VF, H$_2$C=CHF)
perfluoro(ethyl vinyl ether) (PEVE, F$_2$C=CF—OCF$_2$CF$_3$)
perfluoro(propyl vinyl ether) (PPVE, F$_2$C=CF—OCF$_2$CF$_2$CF$_3$)
2-bromo-1,1-difluoroethylene (R-1122B1, F$_2$C=CHBr)
chlorodifluoroethylene (CFE)
dichlorodifluoroethylene (DCFE, F$_2$C=CCl$_2$)
1,1,3,3,3-pentafluoropropene (R-1225zc, F$_2$C=CH—CF$_3$)
1,1,2,3,4,4-hexafluoro-1,3-butadiene (FC 2316, F$_2$C=CF—CF=CF$_2$)
1,1,3,3,3-pentafluoro-2-(trifluoromethyl)prop-1-ene (PFIB, F$_2$C=C(CF$_3$)$_2$) and derivatives thereof.

Thus, advantageously, in this second embodiment, the fluorinated α,ω-bis-azide oligomer of formula (III) is best represented by the formula (VI):

$$N_3-CHR_1CHR_2-(CR_{a1}R_{b1}CR_{c1}R_{d1})_{n1}-\ldots\\-(CR_{ai}R_{bi}CR_{ci}R_{di})_{ni}-(CF_2)_r-(CR_{ci}R_{di}CR_{ai}R_{bi})_{ni}-\ldots-(CR_{c1}R_{d1}CR_{a1}R_{b1})_{n1}-\\CHR_2CHR_1-N_3 \quad (VI),$$

wherein $R_1$ and $R_2$ are as defined above,
r is 2 to 8, and is preferably 4,
i is 1 to 20, preferably 1 to 5, more preferably 1 to 3 or 1 to 2,
$CR_{a1}R_{b1}CR_{c1}R_{d1}$ to $CR_{ai}R_{bi}CR_{ci}R_{di}$ are constitutive moieties, which may be identical or different, derived from monomers independently selected from the fluorinated olefins listed above (i.e., olefins $CR_{a1}R_{b1}=CR_{c1}R_{d1}$ to $CR_{ai}R_{bi}=CR_{ci}R_{di}$, which may be identical or different, are selected from the fluorinated olefins listed above), and
$n_1$ to $n_i$ are each independently a number selected from 1 to 20, preferably 1 to 5.

Advantageously, $R_1$ is a hydrogen atom and $R_2$ is selected from a hydrogen atom, a methyl or a vinyl, or $R_2$ is a hydrogen atom and $R_1$ is selected from a hydrogen atom, a methyl or a vinyl. Preferably, $R_2$ is a hydrogen atom and $R_1$ is selected from a hydrogen atom, a methyl or a vinyl.

For example, in this second embodiment, the fluorinated α,ω-bis(azide) oligomer of formula (VI) is obtained by iodine transfer polymerization (ITP) of the compound I—C$_4$F$_8$—I and two fluorinated olefins, VDF and PMVE, and may be represented by the formula (VII):

$$N_3-CHR_1CHR_2-(CF_2CH_2)_{n1}-(CF(OCF_3)CF_2)_{n2}-(CF_2)_4-(CF_2CF(OCF_3))_{n2}-(CH_2CF_2)_{n1}-CHR_2CHR_1-N_3 \quad (VII),$$

wherein $R_1$ and $R_2$ are as defined above, and
$n_1$ is 1 to 20, and $n_2$ is 1 to 20.

Advantageously, in formula (VII), $R_1$ is a hydrogen atom and $R_2$ is selected from a hydrogen atom, a methyl or a vinyl, or $R_2$ is a hydrogen atom and $R_1$ is selected from a hydrogen atom, a methyl or a vinyl. Preferably, $R_1$ is a hydrogen atom and $R_2$ is selected from a hydrogen atom, a methyl or a vinyl.

Preferably, the fluorinated α,ω-bis(azide) oligomer of formula (VI) or (VII) has a number-average molar mass ($M_n$) of 500 to 8000 g/mol, more preferably 2000 to 4000 g/mol, most preferably 1000 to 2000 g/mol. For example, the fluorinated α,ω-bis(azide) oligomer of formula (VI) has a number-average molar mass ($M_n$) of about 4000 g/mol.

In particular, in this second embodiment, the fluorinated α,ω-bis(propargyl) oligomer (iii) of formula (VI) is obtained by:
1) iodine transfer polymerization (ITP) of the compound I—C$_r$F$_{2r}$—I with r being 2 to 8 (preferably 4) and one or more (preferably 2 or 3) fluorinated olefins selected from:
tetrafluoroethylene (TFE, F$_2$C=CF$_2$)
vinylidene fluoride (VDF, H$_2$C=CF$_2$)
hexafluoropropylene (HFP, F$_2$C=CF—CF$_3$)
trifluoroethylene (TrFE, F$_2$C=CHF)

perfluoro(methyl vinyl ether) (PMVE, $F_2C=CF-OCF_3$)
3,3,3-trifluoropropene (TFP, $H_2C=CH-CF_3$)
2,3,3,3-tetrafluoropropene (R-1234yf, $H_2C=CF-CF_3$)
1,3,3,3-tetrafluoropropene (R-1234ze, trans $FHC=CH-CF_3$)
chlorotrifluoroethylene (CTFE, $F_2C=CFCl$)
bromotrifluoroethylene (BTFE, $F_2C=CFBr$)
iodotrifluoroethylene (ITFE, $F_2Cr-CFI$)
2-chloro-3,3,3-trifluoropropene (1233xf, $H_2C=CCl-CF_3$)
vinyl fluoride (VF, $H_2C=CHF$)
perfluoro(ethyl vinyl ether) (PEVE, $F_2C=CF-OCF_2CF_3$)
perfluoro(propyl vinyl ether) (PPVE, $F_2C=CF-OCF_2CF_2CF_3$)
2-bromo-1,1-difluoroethylene (R-1122B1, $F_2C=CHBr$)
chlorodifluoroethylene (CFE)
dichlorodifluoroethylene (DCFE, $F_2C=CCl_2$)
1,1,3,3,3-pentafluoropropene (R-1225zc, $F_2C=CH-CF_3$)
1,1,2,3,4,4-hexafluoro-1,3-butadiene (FC 2316, $F_2C=CF-CF=CF_2$)
1-propene, 1,1,3,3,3-pentafluoro-2-(trifluoromethyl)-1-propene (PFIB, $F_2C=C(CF_3)_2$)
and derivatives thereof;

2) homologation reaction using a non-fluorinated olefin of formula $CHR_1=CHR_2$, wherein $R_1$ and $R_2$ are as defined above; and 3) azidation, preferably in the presence of $NaN_3$.

Preferably, for step 2), the non-fluorinated olefin of formula $CHR_1=CHR_2$ is selected from ethylene, propylene and butadiene, advantageously ethylene.

Thus, in the particular case where step 1) is carried out using two olefins, VDF and PMVE, and step 2) is carried out with ethylene, the synthesis scheme is presented below. The ITP and ethylenation steps are described in particular in *Macromolecules* 2010, 43, 3652-3663 and *Macromolecules* 2012, 45, 7375-7387.

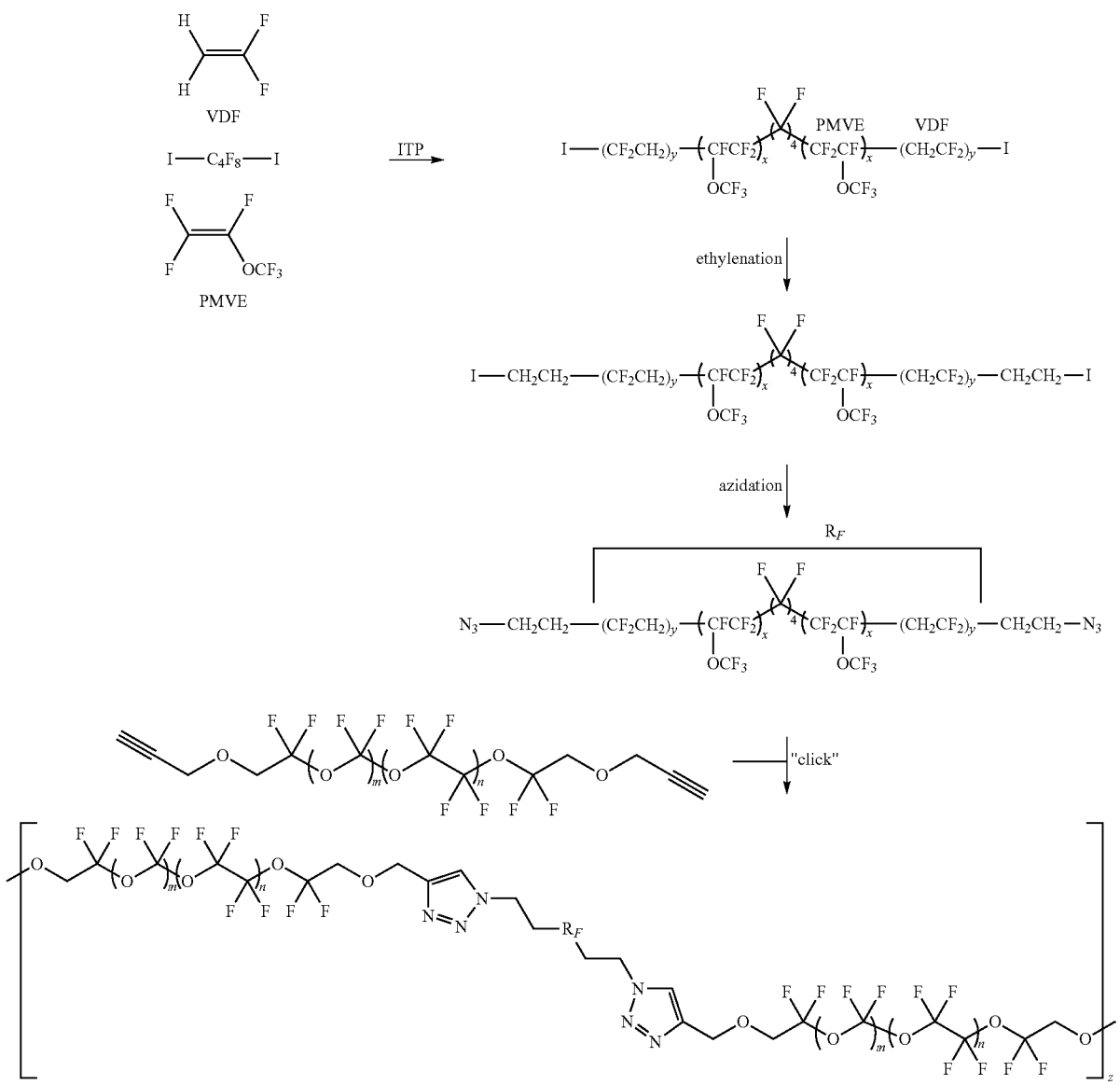

Furthermore, the fluorinated α,ω-bis-azide oligomer may be a mixture of fluorinated α,ω-bis-azide oligomers derived from the two embodiments above. Thus, in particular, the fluorinated α,ω-bis-azide oligomer (iii) of formula (IV) may be a mixture of oligomers of formula (V) and/or (VI), in any proportions.

Preferred Embodiments

In a particular embodiment, the cross-linkable composition according to the invention comprises:
i) a fluorinated α,ω-bis(propargyl) oligomer of formula (I) as defined above, advantageously with p=0 or p=1.75; and
ii) a cross-linking agent comprising three azide ($—N_3$) groups, notably of formula (II) as defined above, preferably with $R_3$ being a hydrogen atom and Y being OH, $OCH_2CH_2P(O)(OH)_2$ or $OCH_2CH_2P(O)(OCH_3)_2$; notably it is pentaerythritol triazide.

In another particular embodiment, the cross-linkable composition according to the invention comprises:
i) a fluorinated α,ω-bis(propargyl) oligomer of formula (I) as defined above, advantageously with p=0 or p=1.75;
ii) a cross-linking agent comprising three azide ($—N_3$) groups, advantageously of formula (II) as defined above, preferably with $R_3$ being a hydrogen atom and Y being OH, $OCH_2CH_2P(O)(OH)_2$ or $OCH_2CH_2P(O)(OCH_3)_2$; notably it is pentaerythritol triazide; and
iii) a fluorinated α,ω-bis(azide) oligomer selected from the oligomers of formula (V) as defined above, with p' typically being 0 or 1.75. Preferably, p and p' are identical.

In another particular embodiment, the cross-linkable composition according to the invention comprises:
i) a fluorinated α,ω-bis(propargyl) oligomer of formula (I) as defined above, advantageously with p=0 or p=1.75;
ii) a cross-linking agent comprising three azide ($—N_3$) groups, advantageously of formula (III) as defined above, preferably, with $R_3$ being a hydrogen atom and Y being OH, $OCH_2CH_2P(O)(OH)_2$ or $OCH_2CH_2P(O)(OCH_3)_2$; notably it is pentaerythritol triazide; and
iii) a fluorinated α,ω-bis(azide) oligomer selected from the oligomers of formula (VI) as defined above.

In these particular embodiments, the respective molar proportions of oligomers (i) and (iii) and of cross-linking agent (ii) are such that the total number of propargyl ($—CH_2—C≡CH$) groups is equal to the total number of azide ($—N_3$) groups.

Thus, in the first particular embodiment, the respective molar proportions of oligomer (i) and of cross-linking agent (ii) are 3:2.

In the second and third particular embodiments, the relative proportions of cross-linking agent comprising three azide ($—N_3$) groups (ii) and of fluorinated α,ω-bis(azide) oligomer (iii) are for example such that 20, 40, 60 or 80 mol % of the azide ($—N_3$) groups are provided by the crosslinking agent comprising three azide ($—N_3$) groups, relative to the total number of azide groups.

Materials

The present invention is also directed to a material derived from the click-chemistry reaction between:
i) a fluorinated α,ω-bis(propargyl) oligomer of formula (I) as defined above, notably with p being 0 or 1.75;
ii) a cross-linking agent comprising at least three azide ($—N_3$) groups notably of formula (III) as defined above; and
iii) optionally, a fluorinated oligomer comprising two terminal azide ($—N_3$) groups (also called fluorinated α,ω-bis(azide) oligomer).

In other words, the material according to the invention comprises or consists of the product of the click-chemistry reaction of the cross-linkable composition according to the invention.

Preferably, the click-chemistry reaction is carried out in the presence of a copper catalyst, such as a copper(I) salt.

The particular, advantageous and preferred embodiments of the material according to the invention are identical to those of the cross-linkable composition according to the invention, notably with regard to the definition of oligomers (i) and (iii) and of cross-linking agent (ii), and of the respective molar proportions thereof.

Notably, in a preferred embodiment, the material according to the invention comprises the product of the click-chemistry reaction between:
i) a fluorinated α,ω-bis(propargyl) oligomer of formula (I) as defined above, notably with p being 0 or 1.75; and
ii) a cross-linking agent comprising three azide ($—N_3$) groups, advantageously of formula (III) as defined above, preferably, with $R_3$ being a hydrogen atom and Y being OH, $OCH_2CH_2P(O)(OH)_2$ or $OCH_2CH_2P(O)(OCH_3)_2$; notably it is pentaerythritol triazide.

In another preferred embodiment, the material according to the invention comprises the product of the click-chemistry reaction between:
i) a fluorinated α,ω-bis(propargyl) oligomer of formula (I) as defined above, notably with p being 0 or 1.75;
ii) a cross-linking agent comprising three azide ($—N_3$) groups, advantageously of formula (III) as defined above, preferably, with $R_3$ being a hydrogen atom and Y being OH, $OCH_2CH_2P(O)(OH)_2$ or $OCH_2CH_2P(O)(OCH_3)_2$; notably it is pentaerythritol triazide; and
iii) a fluorinated α,ω-bis(azide) oligomer selected from the oligomers of formula (IV) as defined above, notably with p' being 0 or 1.75. Preferably, p and p' are identical.

In another preferred embodiment the material according to the invention comprises the product of the click-chemistry reaction between:
i) a fluorinated α,ω-bis(propargyl) oligomer of formula (I) as defined above, notably with p being 0 or 1.75;
ii) a cross-linking agent comprising three azide ($—N_3$) groups, advantageously of formula (III) as defined above, preferably, with being a hydrogen atom and Y being OH, $OCH_2CH_2P(O)(OH)_2$ or $OCH_2CH_2P(O)(OCH_3)_2$; notably it is pentaerythritol triazide; and
iii) a fluorinated α,ω-bis(azide) oligomer selected from the oligomers of formula (V) and/or (VI) as defined above.

The respective molar proportions of compounds (i), (ii) and (iii) in order to obtain the material according to the invention are such that the total number of propargyl ($—CH_2—C≡CH$) groups is equal to the total number of azide ($—N_3$) groups.

Thus, in the first particular embodiment, the respective molar proportions of compounds (i) and (ii) are 3:2.

In the second and third particular embodiments, the relative proportions of cross-linking agent comprising three azide ($—N_3$) groups (ii) and of fluorinated α,ω-bis(azide) oligomer (iii) are for example such that 20, 40, 60 or 80 mol % of the azide ($—N_3$) groups are provided by the cross-linking agent comprising three azide ($—N_3$) groups, relative to the total number of azide groups.

As indicated above, the properties of the materials according to the invention can be modulated as desired as a function of the length and nature of the fluorinated chain of the α,ω-bis(azide) oligomer and of the molar proportion of cross-linking agent in the starting cross-linkable composition. In particular, the effects of variations of molar proportions of cross-linking agent in the starting cross-linkable composition on the structure of the material are explained schematically in FIG. 16. Recall that, advantageously, in each formulation, the total number of azide groups provided either by the fluorinated chain of the α,ω-bis(azide) oligomer or by the cross-linking agent is always equal to the number of propargyl groups provided by the fluorinated am bis(propargyl) oligomer.

Thus, the materials according to the present invention are comparable to thermosetting materials or to elastomers, notably as a function of the mesh density of their three-dimensional network.

For example, a small amount of triazide cross-linking agent makes it possible to produce a highly flexible polymer matrix which ceases to flow once cross-linked. This type of material is notably sought for the production of highly flexible encapsulants useful for protecting electronic components containing fragile wiring and soldering.

An increasing proportion of triazide cross-linking agent induces a polymer network with a higher density of cross-linking points (see FIG. 16), and thus a higher mechanical stiffness which will be more suited to the production of elastomeric joints.

Thus, when a thermosetting material is sought, one will select in particular a material according to the invention wherein the relative proportions of cross-linking agent comprising three azide (—$N_3$) groups (ii) and of fluorinated α,ω-bis(azide) oligomer (iii) are such that at least 20 mol %, in particular 20 to 80 mol %, of the azide (—$N_3$) groups are provided by the cross-linking agent comprising three azide (—$N_3$) groups, relative to the total number of azide groups. A fluorinated α,ω-bis(azide) oligomer (iii) of formula (VI) as defined above will also preferably be selected.

In particular, the materials consisting of cross-linking agent (ii) and of fluorinated α,ω-bis(propargyl) oligomer (i) are thermosetting materials.

Conversely, when a flexible material (or elastomer) is sought, one will select in particular a material according to the invention wherein the relative proportions of cross-linking agent comprising three azide (—$N_3$) groups (ii) and of fluorinated α,ω-bis(azide) oligomer (iii) are such that at most 20 mol %, notably 5 to 20 mol %, of the azide (—$N_3$) groups are provided by the cross-linking agent comprising three azide (—$N_3$) groups, relative to the total number of azide groups. In this case, the fluorinated α,ω-bis(azide) oligomer (iii) is not optional. A fluorinated α,ω-bis(azide) oligomer (iii) of formula (V) as defined above, or a fluorinated α,ω-bis(azide) oligomer (iii) of formula (VI) with a long chain-length, will be preferred.

The material according to the invention, whether comparable to a thermoset or an elastomer, comprises, in addition to the fluorinated moieties described for oligomers (i) and (iii) and the cross-linking agent moiety (ii), disubstituted 1,2,3-triazole moieties, and in particular 1,4-disubstituted 1,2,3-triazole. The 1,2,3-triazole moieties being of heteroaromatic nature and not very chemically reactive, they are involved, alongside the fluorinated moieties, in the chemical stability of the materials according to the invention, notably in harsh environments and/or at high temperatures, notably at a temperature above 250° C., even 300° C., for example at a temperature of 250° C. to 350° C.

The material according to the invention advantageously has a decomposition temperature at 10% weight loss ($T_d^{10\%}$) in air of 250° C. or higher, preferably 275° C. or higher, more preferably 280° C. or higher, most preferably 300° C. or higher. For example, the material according to the invention has a $T_d^{10\%}$ of 250° C. to 400° C., preferably 250° C. to 350° C.

The material according to the invention advantageously has at least one glass-transition temperature value ($T_{g1}$) of −70° C. or lower, preferably −80° C. or lower, most preferably −100° C. or lower. This glass-transition value is selected as a function of the applications envisaged for the polymer. For example, the polymeric material according to the invention has a $T_{g1}$ of −150° C. to −70° C., preferably −120° C. to −85° C.

Process for Synthesizing the Polymers According to the Invention

The present invention also concerns a process for preparing the material according to the invention.

The process according to the invention is based on a click-chemistry reaction which has the triple advantage of having high or even quantitative yield, having high kinetics, and not producing any harmful or toxic by-products. Owing to these features, the process according to the invention is easy to industrialize.

Within the meaning of the present invention, high yield is a yield of 90% or higher, advantageously 95% or higher. A quantitative yield is a yield of 100%.

Furthermore, the process according to the invention is highly modular and very easy to implement. Indeed, the fluorinated oligomers (i) and optionally (iii), and the cross-linking agent (ii), are prepared upstream, completely independently of the click-chemistry copolymerization reaction, this last step which may be carried out at a later stage. This is particularly advantageous insofar as, notably in the case of the fluorinated α,ω-bis(azide) oligomers of formula (VI), the starting products are mostly gaseous.

Thus, the process for preparing the material according to the invention comprises a step of cross-linking by click chemistry between:

i) a fluorinated α,ω-bis(propargyl) oligomer of formula (I) as defined above, notably with p being 0 or 1.75;

ii) a cross-linking agent comprising at least three azide (—$N_3$) groups; advantageously of formula (III) as defined above and iii) optionally, a fluorinated oligomer comprising two terminal azide (—$N_3$) groups (also called fluorinated α,ω-bis(azide) oligomer).

In other words, the process for preparing the material according to the invention comprises a step of cross-linking by click chemistry of the cross-linkable composition of the invention.

The particular, advantageous and preferred embodiments of the process according to the invention are identical to those of the cross-linkable composition according to the invention, notably with regard to the definition of oligomers (i) and (iii), of cross-linking agent (ii), and of the respective molar proportions thereof.

Schematically, in a particular embodiment, the process according to the invention implements the following reaction:

Cross-linkable composition according to the invention (particular embodiment)

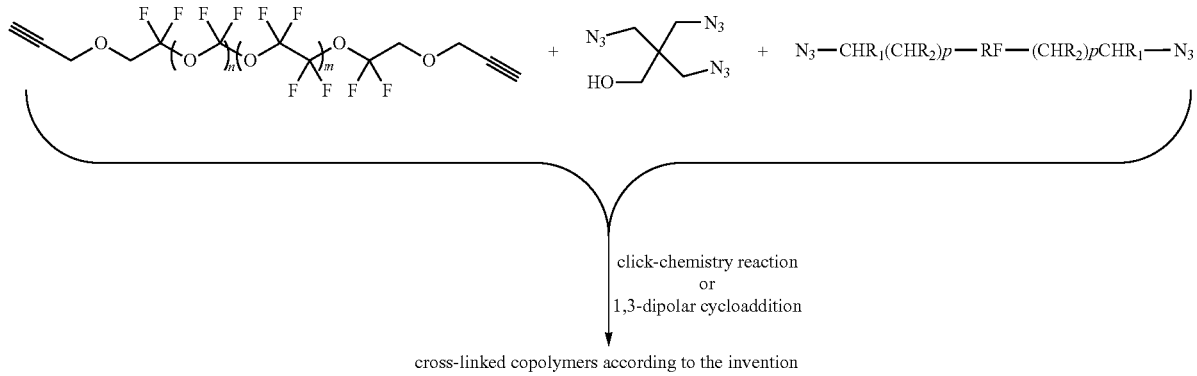

Cross-linking by click chemistry between a fluorinated α,ω-bis(propargyl) oligomer, pentaerythritol triazide, and a fluorinated α,ω-bis(azide) oligomer.

Advantageously, the respective molar proportions of compounds (i), (ii) and (iii) are such that the total number of propargyl (—CH$_2$—C≡CH) groups is equal to the total number of azide (—N$_3$) groups.

As the click-chemistry reaction has a very high or even quantitative yield, such molar proportions make it possible in particular to ensure total consumption of the reactive species during implementation of the process according to the invention.

For example, the relative proportions of cross-linking agent comprising three azide (—N$_3$) groups (ii) and of fluorinated α,ω-bis(azide) oligomer (iii) are such that 20 mol % of the azide (—N$_3$) groups are provided by the cross-linking agent comprising three azide (—N$_3$) groups, relative to the total number of azide groups. In other words, 1.5 moles of (i) per 0.2 moles of (ii) and 1.2 moles of (iii) will be used.

In a second example, the relative proportions of cross-linking agent comprising three azide (—N$_3$) groups (ii) and of fluorinated α,ω-bis(azide) oligomer (iii) are such that 40 mol % of the azide (—N$_3$) groups are provided by the cross-linking agent comprising three azide (—N$_3$) groups, relative to the total number of azide groups. In other words, 1.5 moles of (i) per 0.4 moles of (ii) and 0.9 moles of (iii) will be used.

In a third example, the relative proportions of cross-linking agent comprising three azide (—N$_3$) groups (ii) and of fluorinated α,ω-bis(azide) oligomer (iii) are such that 60 mol % of the azide (—N$_3$) groups are provided by the cross-linking agent comprising three azide (—N$_3$) groups, relative to the total number of azide groups. In other words, 1.5 moles of (i) per 0.6 moles of (ii) and 0.6 moles of (iii) will be used.

In a fourth example, the relative proportions of cross-linking agent comprising three azide (—N$_3$) groups (ii) and of fluorinated α,ω-bis(azide) oligomer (iii), are such that 80 mol % of the azide (—N$_3$) groups are provided by the cross-linking agent comprising three azide (—N$_3$) groups, relative to the total number of azide groups. In other words, 1.5 moles of (i) per 0.8 moles of (ii) and 0.3 moles of (iii) will be used.

The cross-linking by click chemistry is preferably carried out in the presence of a copper catalyst, preferably a copper(I) or (II) salt. Preferably, a copper(I) salt such as a salt of formula CuX, X being a triflate group or a halogen atom, notably chlorine, bromine or iodine, will be used. Most preferably, copper bromide or chloride will be used. The catalyst is advantageously used in an amount of 0.001 molar equivalents to 0.2 molar equivalents, preferably 0.01 to 0.15 molar equivalents, relative to the number of moles of the α,ω-bis(propargyl) oligomer (i). Furthermore, the copper salt is preferably used in combination with a ligand to improve the reactivity and/or stability thereof, preferably a polyamine, such as a triamine or a linear or cyclic tetramine, or in the presence of a pyridine derivative. By way of example of a copper ligand, mention may be made of 1,1,4,7,7-pentamethyldiethylenetriamine (also called N,N,N',N',N''-pentamethyldiethylenetriamine or PMDETA), 1,4,7,10-tetraazacyclododecane, 1,1,4,7,10,10-hexamethyltriethylenetetramine (HMTETA), tris(2-pyridylmethyl)amine (TPMA), tris[2-(dimethylamino)ethyl]amine (Me$_6$TREN), 2,2'-bipyridyl (bpy), 4,4'-dinonyl-2,2'-dipyridyl (dNbpy), 2,2':6',2''-terpyridine (tpy), tris[(1-benzyl-1H-1,2,3-triazol-4-yl)methyl]amine (TBTA), and tris(3-hydroxypropyltriazolylmethyl)amine (THPTA).

Preferably, the ligand is 1,1,4,7,7-pentamethyldiethylenetriamine. The ligand is advantageously used in an amount of 0.001 molar equivalents to 0.2 molar equivalents, preferably 0.01 to 0.15 molar equivalents, relative to the number of moles of the α,ω-bis(propargyl) oligomer (i). In a particular embodiment, the amount of ligand and of copper catalyst in molar equivalents is identical.

Thus, a salt of formula CuX, X being a triflate group or a halogen atom, in particular chlorine or bromine, will preferably be used in combination with 1,1,4,7,7-pentamethyldiethylenetriamine.

In a particular embodiment, the catalyst is supported on a solid support, and is advantageously recyclable.

In a particular embodiment, the process according to the invention is carried out in the absence of solvent, notably to avoid any contamination by copper residues. In this case, at least one of oligomers (i) or (iii) or cross-linking agent (ii) plays the role of solvent.

In another particular embodiment, the process according to the invention is carried out in a solvent capable of solubilizing oligomers (i) and (iii) and cross-linking agent (ii). Preferably, the solvent is aprotic and polar. However, the solvent must not interact deleteriously with copper. For example, the use of solvents derived from pyridine will thus be avoided. Preferably, the solvent used is selected from DMF, DMSO or acetone; advantageously it is DMF.

The cross-linking by click-chemistry reaction of the process according to the invention is preferably carried out at atmospheric pressure and at a temperature of 15° C. to 200° C., more preferably 18° C. to 180° C. In a particular embodiment, the reaction temperature is 18° C. to 25° C. In another embodiment, the reaction temperature is 100° C. to 200° C., preferably 140° C. to 180° C.

Particular Embodiments

In a particular embodiment, the process for preparing the material according to the invention comprises a step of cross-linking by click chemistry between:
i) a fluorinated α,ω-bis(propargyl) oligomer of formula (I) as defined above, notably with p being 0 or 1.75; and
ii) a cross-linking agent comprising three azide (—N$_3$) groups, advantageously of formula (III) as defined above.

Preferably, in this particular embodiment, the cross-linking agent is of formula (III) as defined above with R$_3$ being a hydrogen atom and Y being OH, OCH$_2$CH$_2$P(O)(OH)$_2$ or OCH$_2$CH$_2$P(O)(OCH$_3$)$_2$; notably it is pentaerythritol triazide. When p is 0, the process according to the invention may then be represented schematically as follows:

the reaction is preferably carried out without solvent. The components of the cross-linkable composition are mixed and then heated to a temperature allowing the click reaction to be carried out, for example about 160° C.

In another particular embodiment, the process for preparing the material according to the invention comprises a step of cross-linking by click chemistry between:
i) a fluorinated α,ω-bis(propargyl) oligomer of formula (I) as defined above, notably with p being 0 or 1.75; and
ii) a compound of formula (III) as defined above with, preferably, R$_3$ being a hydrogen atom and Y being OH, OCH$_2$CH$_2$P(O)(OH)$_2$ or OCH$_2$CH$_2$P(O)(OCH$_3$)$_2$, notably pentaerythritol triazide:

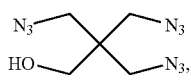

as cross-linking agent; and
iii) a fluorinated α,ω-bis(azide) oligomer of formula (V) as defined above, notably with p' being 0 or 1.75. Preferably, p' is equal to p.

Preferably, in this embodiment, the click-chemistry reaction is carried out at atmospheric pressure and at a tempera-

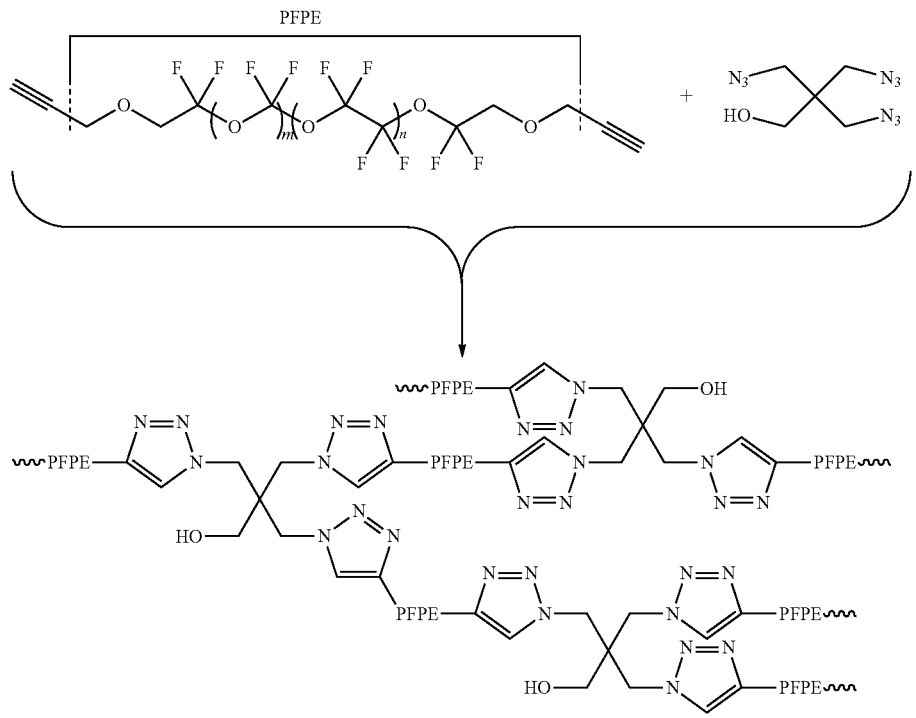

Cross-linking by click chemistry between a fluorinated α,ω-bis(propargyl) oligomer of formula (I) and pentaerythritol triazide.

In this particular embodiment, the process according to the invention is preferably carried out without solvent.

Preferably, in this embodiment, the click-chemistry reaction is carried out at atmospheric pressure and at a temperature of 80° C. to 200° C., preferably 100° C. to 200° C., notably 140° C. to 180° C. Furthermore, in this embodiment, ture of 100° C. to 200° C., preferably 140° C. to 180° C. Furthermore, in this embodiment, the reaction is preferably carried out without solvent. The two or three components of the mixture are mixed and then heated to a temperature allowing the click reaction to be carried out, for example about 160° C.

In a third particular embodiment, the process for preparing the material according to the invention comprises a step of cross-linking by click chemistry between:

i) a fluorinated α,ω-bis(propargyl) oligomer of formula (I) as defined above, notably with p being 0 or 1.75; and ii) a compound of formula (III) as defined above with, preferably, $R_3$, being a hydrogen atom and Y being OH, $OCH_2CH_2P(O)(OH)_2$ or $OCH_2CH_2P(O)(OCH_3)_2$, notably pentaerythritol triazide:

as cross-linking agent; and iii) a fluorinated α,ω-bis(azide) oligomer of formula (VI) as defined above.

Preferably, in this embodiment, the click-chemistry reaction is carried out at atmospheric pressure and at a temperature of 100° C. to 200° C., preferably 140° C. to 180° C. Furthermore, in this embodiment, the reaction is preferably carried out without solvent. The two or three components of the mixture are mixed and then heated to a temperature allowing the click reaction to be carried out, for example about 160° C.

In these three particular embodiments, the respective molar proportions of compounds (i), (ii) and (iii) are such that the total number of propargyl (—$CH_2$—C≡CH) groups is equal to the total number of azide (—$N_3$) groups.

Thus, in the first particular embodiment, the respective molar proportions of compounds (i) and (ii) are 3:2.

In the second and third particular embodiments, the relative proportions of cross-linking agent comprising three azide (—$N_3$) groups (ii) and of fluorinated α,ω-bis(azide) oligomer (iii) are for example such that 20, 40, 60 or 80 mol % of the azide (—$N_3$) groups are provided by the cross-linking agent comprising three azide (—$N_3$) groups, relative to the total number of azide groups.

Uses

The present invention also relates to the use of, the material according to the invention as electrical insulator, notably in harsh environments, and/or at high temperature, particularly at a temperature above 250° C., indeed above 300° C. The possibility of synthesizing and then producing matrices potentially endowed with a low $T_g$ value also permits the use thereof as flexible matrices at temperatures as low as −100° C.

The materials according to the invention are in particular useful in the field of on-board systems as they do not mechanically (due to their flexibility) or chemically (high stability notably in harsh environments and/or at high temperature and/or in humid environments) restrict the electrical or electronic components to be covered with said materials, which act as both protective agents and electrical insulators.

Thus, the materials according to the invention are notably useful as encapsulants for electronic cards in on-board systems or power modules, as coatings for rotary machines or electric motors, as semi-rigid packaging components, and as wiring components.

The materials according to the invention are typically used as sealing elements on aircraft, notably on various airframe components, and include sealing beads, O-rings, body elements or pump wiring components.

Mention may also be made of applications in the chemical engineering sector, in particular the transportation, storage and handling of corrosive products such as hydrocarbons, notably gaskets, reactor coatings or storage containers.

In short, the materials according to the invention have the following advantages:

they are easy to synthesize and use, in particular on an industrial scale, at once in terms of safety (absence of toxic by-products during the cross-linking reaction), reaction kinetics, reaction conditions, yields (the yield of the cross-linking reaction is very high, indeed quantitative), which makes their manufacturing costs acceptable for fluorinated polymers, a high degree of modularity of the properties of the materials, provided notably by the amount of cross-linking agent (ii), and sequence $R_F$ of the fluorinated α,ω-bis(azide) oligomer (iii), making it possible to produce as desired thermosetting or elastomeric materials for various applications as electrical insulators in particular.

PRESENTATION OF THE FIGURES

Z-DOL) and of the α,ω-bis(tosylate) PFPE of step 1 of Example 2. The x-axis represents chemical shifts in ppm.

Figure 10:
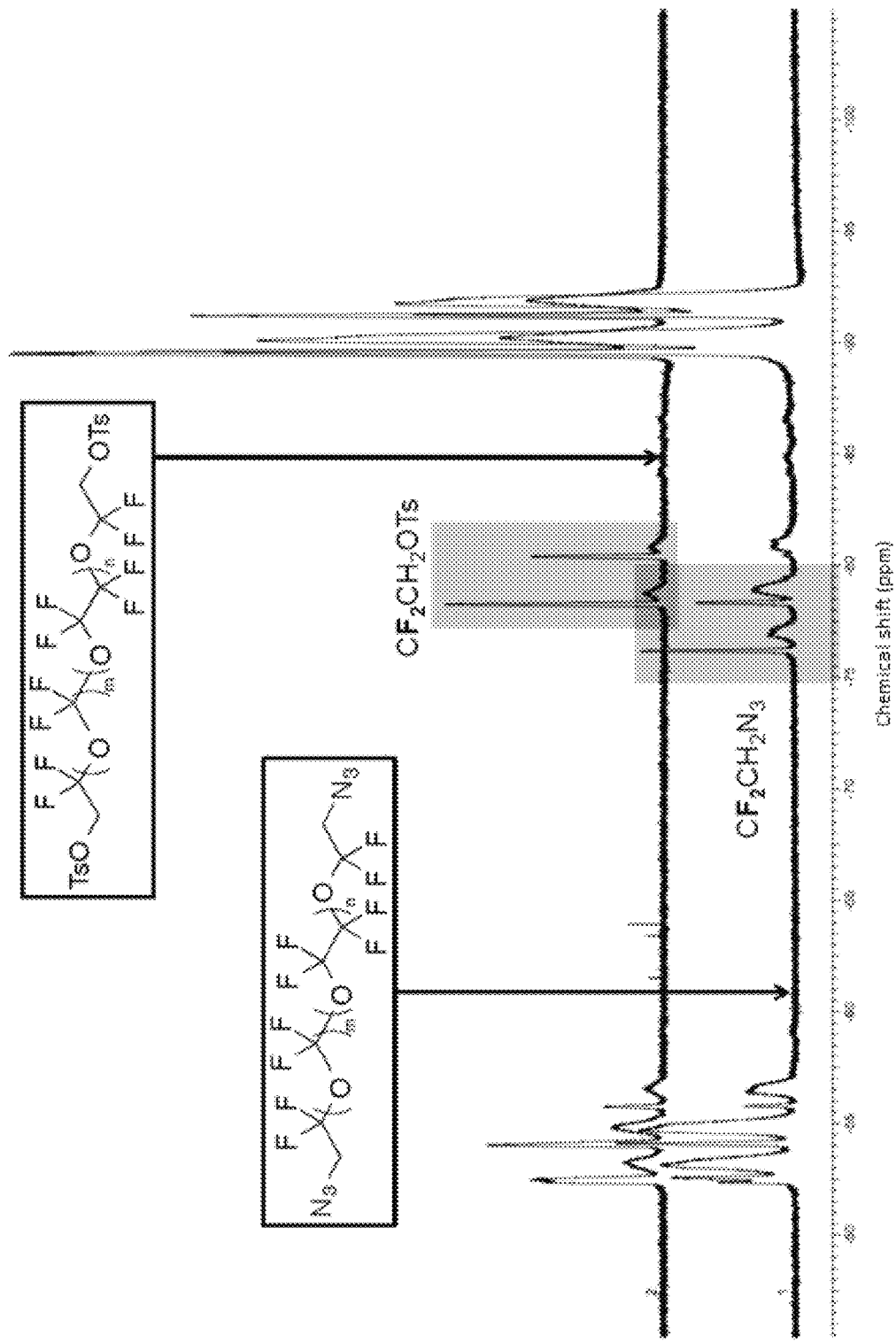

FIG. 10 shows a superposition of the $^{19}$F NMR spectra in deuterated methanol (MeOH-d$_4$) of the α,ω-bis(tosylate) PFPE of step 1 of Example 2 and the α,ω-bis(azido) PFPE of step 2 of Example 2. The x-axis represents chemical shifts in ppm.

Figure 11:
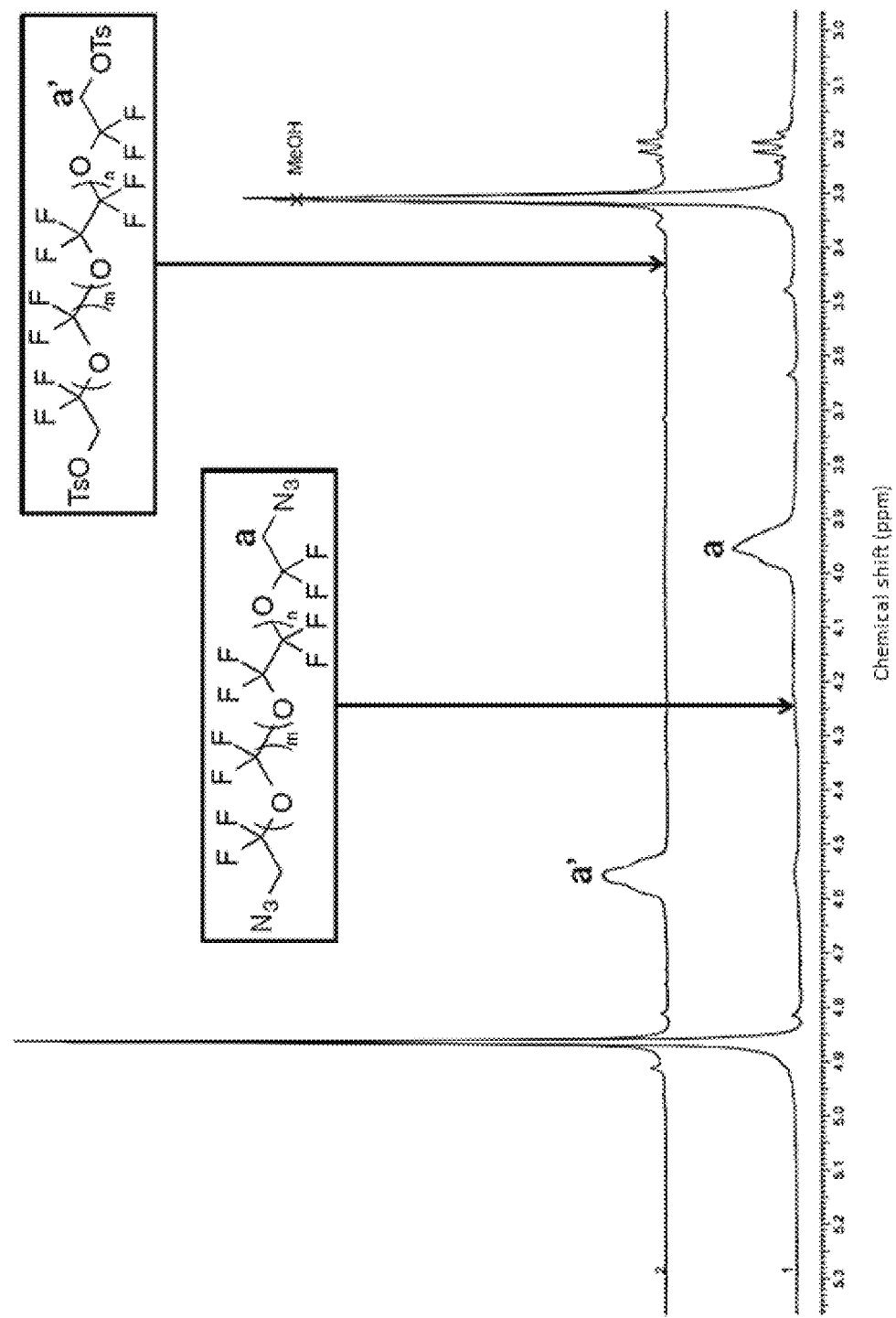

FIG. 11 shows a superposition of the $^1$H NMR spectra in deuterated methanol (MeOH-d$_4$) of the α,ω-bis(tosylate) PFPE of step 1 of Example 2 and the α,ω-bis(azido) PFPE of step 2 of Example 2. The x-axis represents chemical shifts in ppm.

Figure 12:
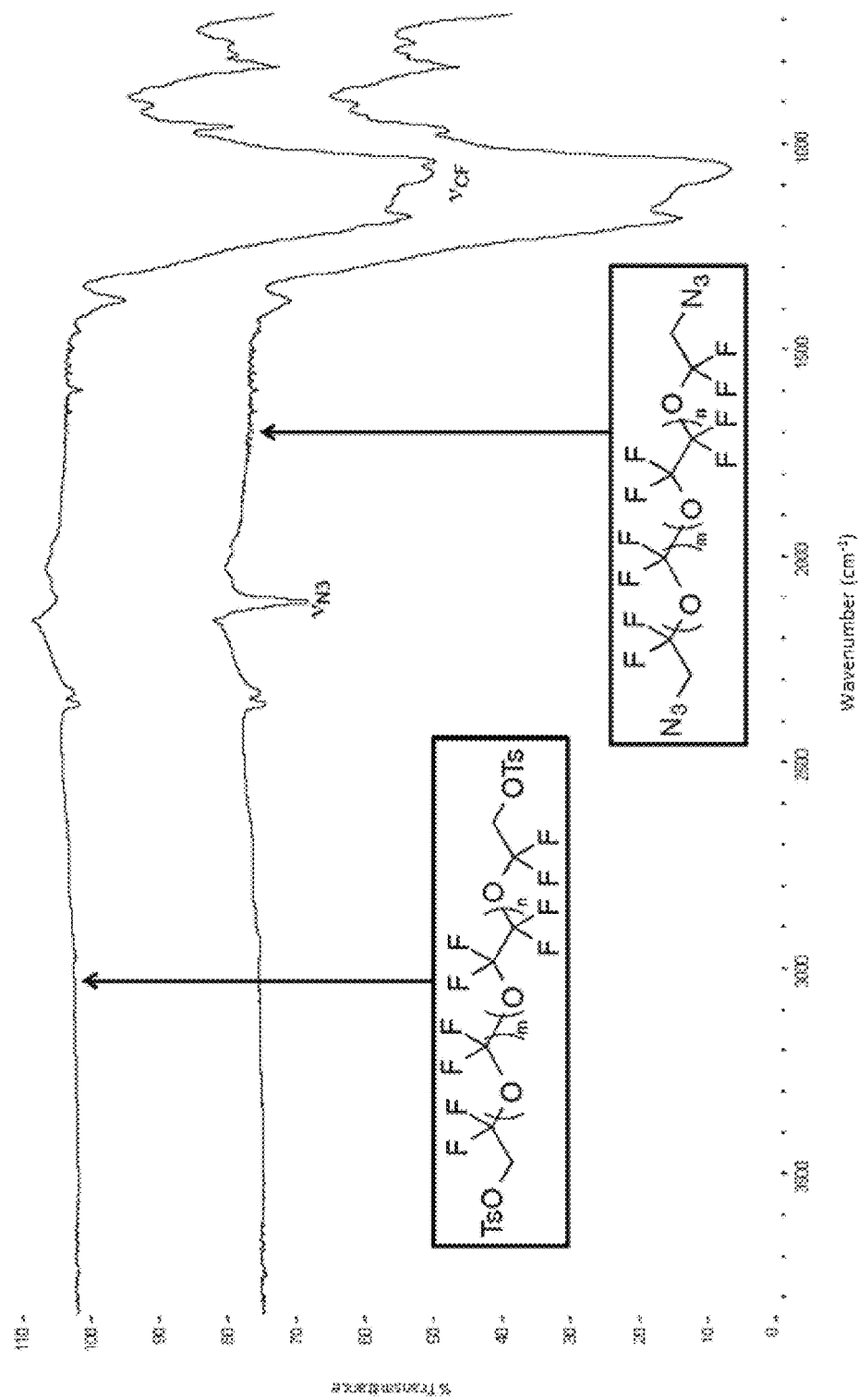

FIG. 12 shows a superposition of the FTIR spectra of the α,ω-bis(tosylate) PFPE of step 1 of Example 2 and the α,ω-bis(azido) PFPE of step 2 of Example 2. The x-axis represents wavenumber cm$^{-1}$) and the y-axis represents transmittance (in %).

Figure 13:
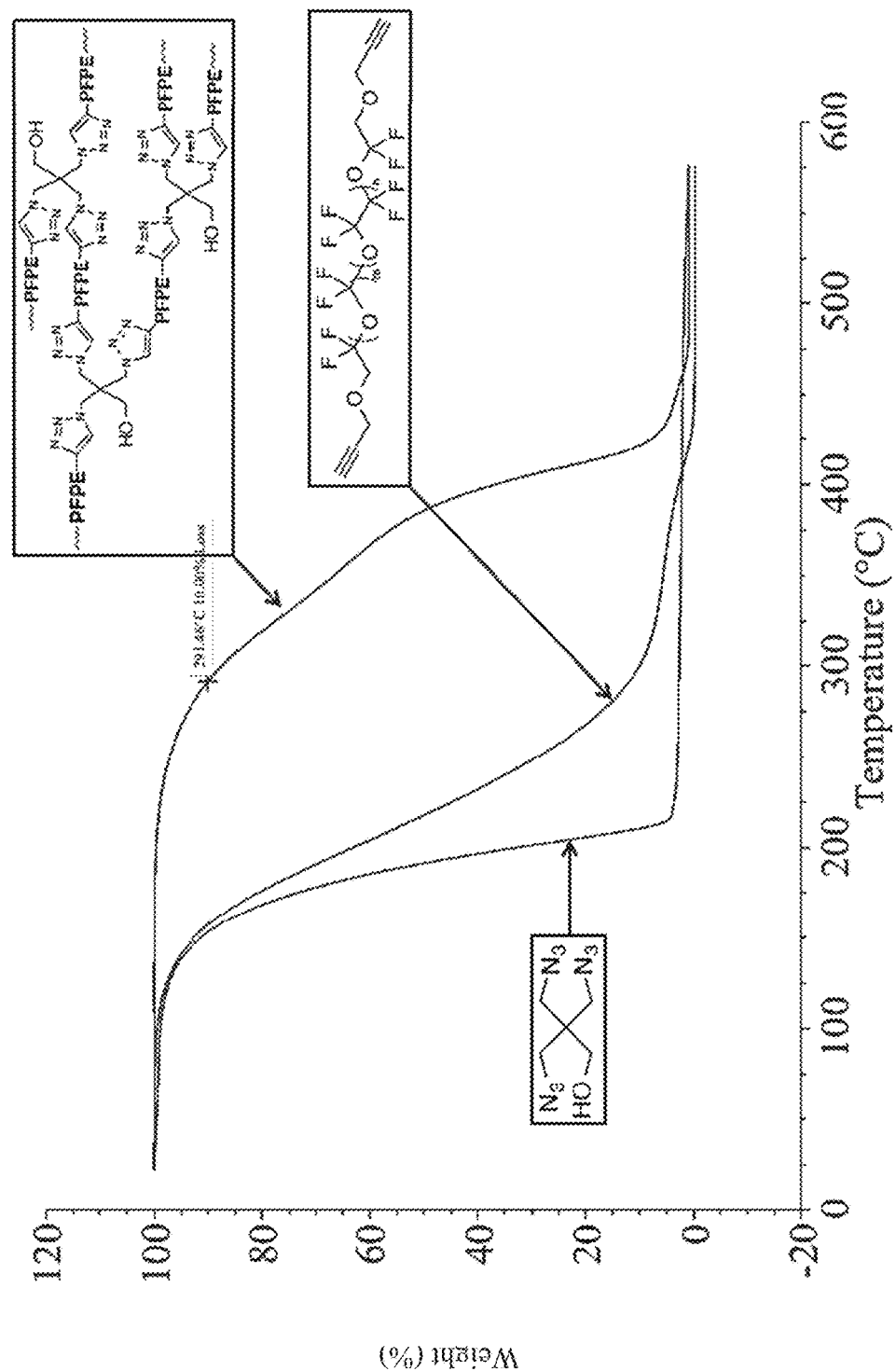

FIG. 13 shows a superposition of the thermogravimetric analysis (TGA) thermograms at 10° C. per minute in air, of the "ternary" material of Example 7.2 and the precursors thereof, the pentaerythritol triazide of Example 5, and the PFPE-dialkyne ether of Example 1. The x-axis represents temperature (in ° C.), and the y-axis represents weight (in %).

Figure 14:
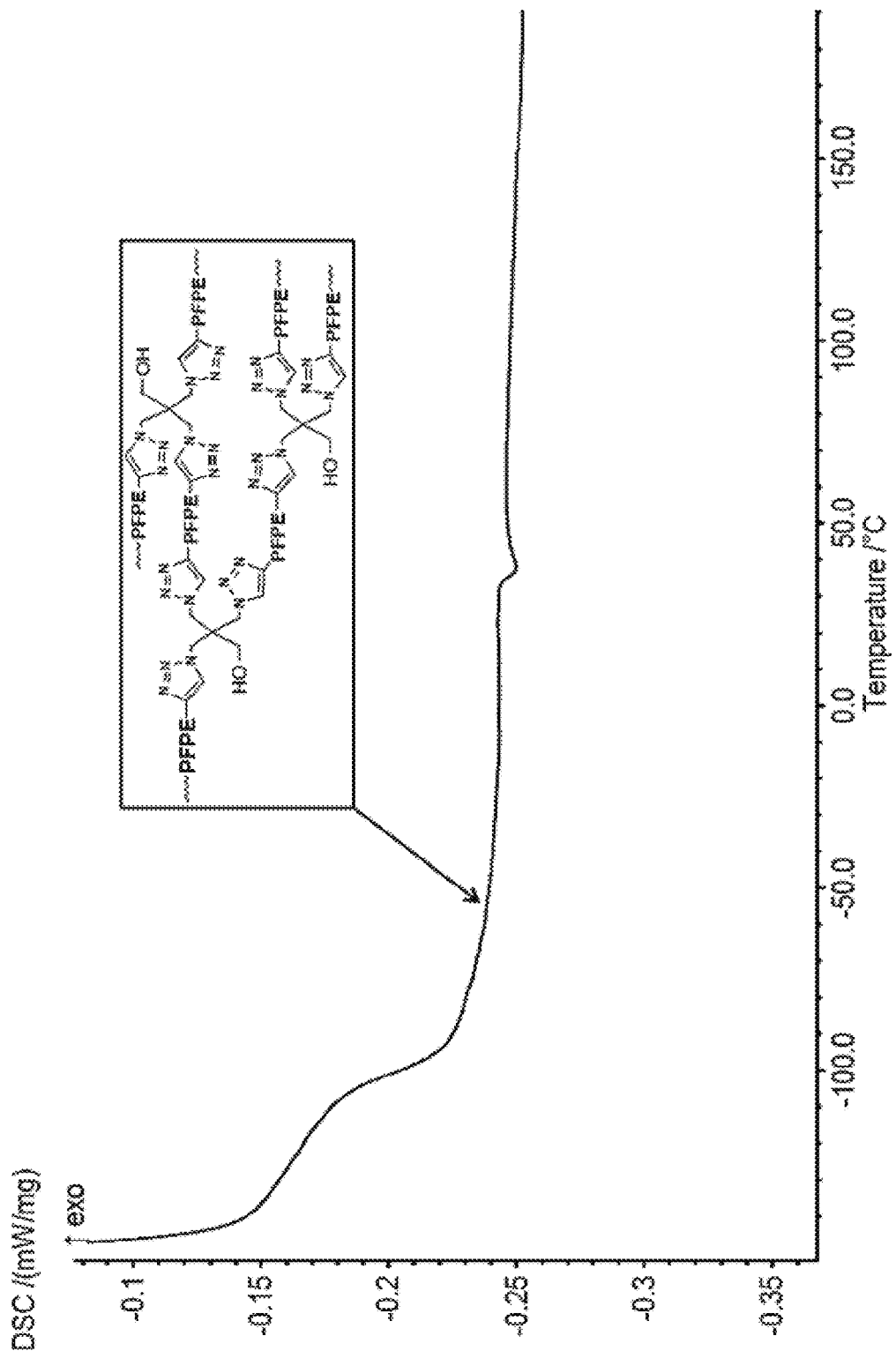

FIG. 14 shows the differential scanning calorimetry (DSC) analysis thermogram of the "ternary" material of Example 7.2. The x-axis represents temperature (in ° C.), and the y-axis represents heat flow (in mW/mg).

Figure 15:
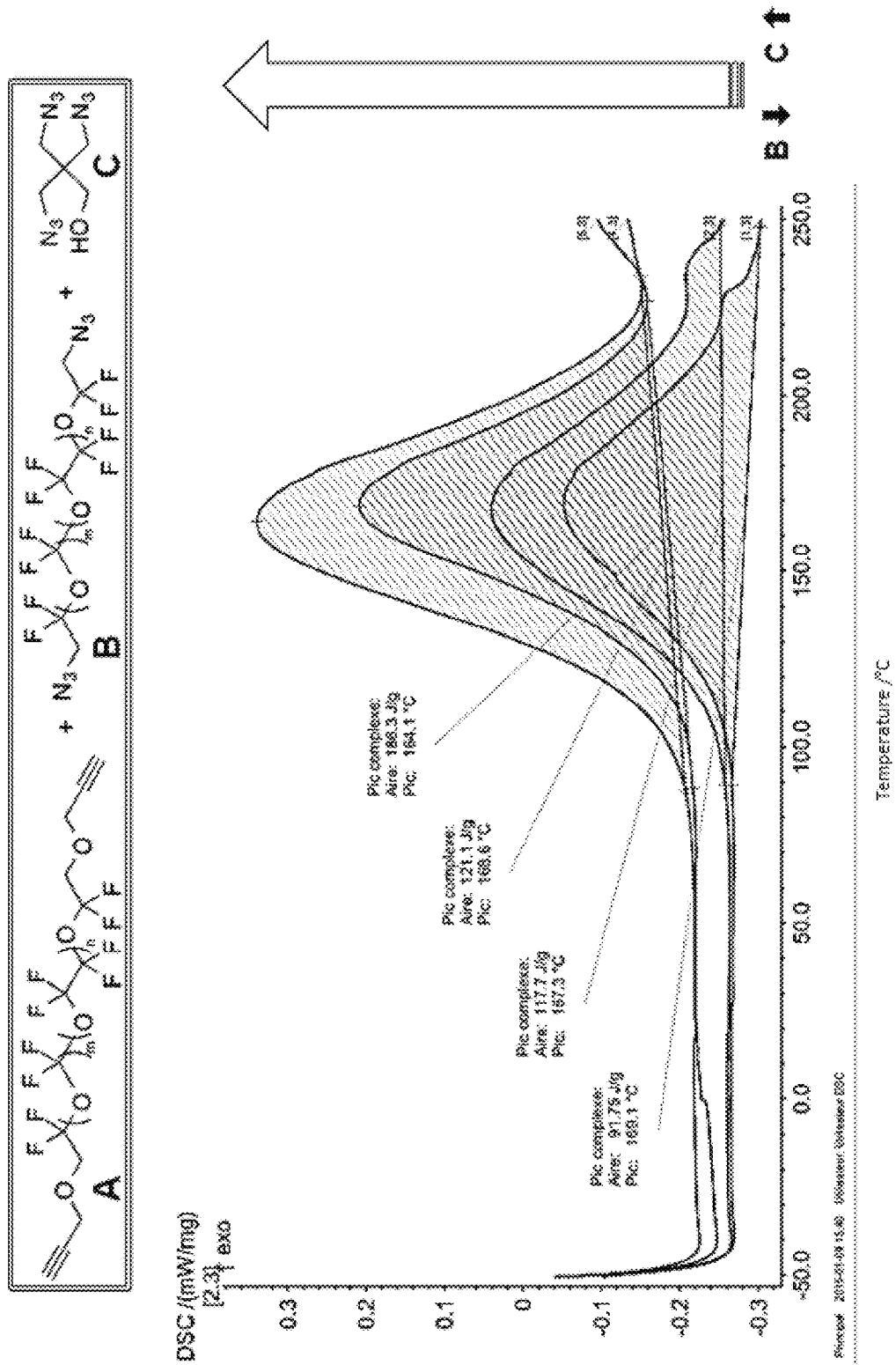

FIG. 15 shows the differential scanning calorimetry (DSC) analysis thermogram of the "ternary" materials LG-75, LG-76, LG-77 and LG-78 of Example 7.3. The enthalpy of cross-linking is given in J/g. The x-axis represents temperature (in ° C.), and the y-axis represents heat flow (in mW/mg).

Figure 16:
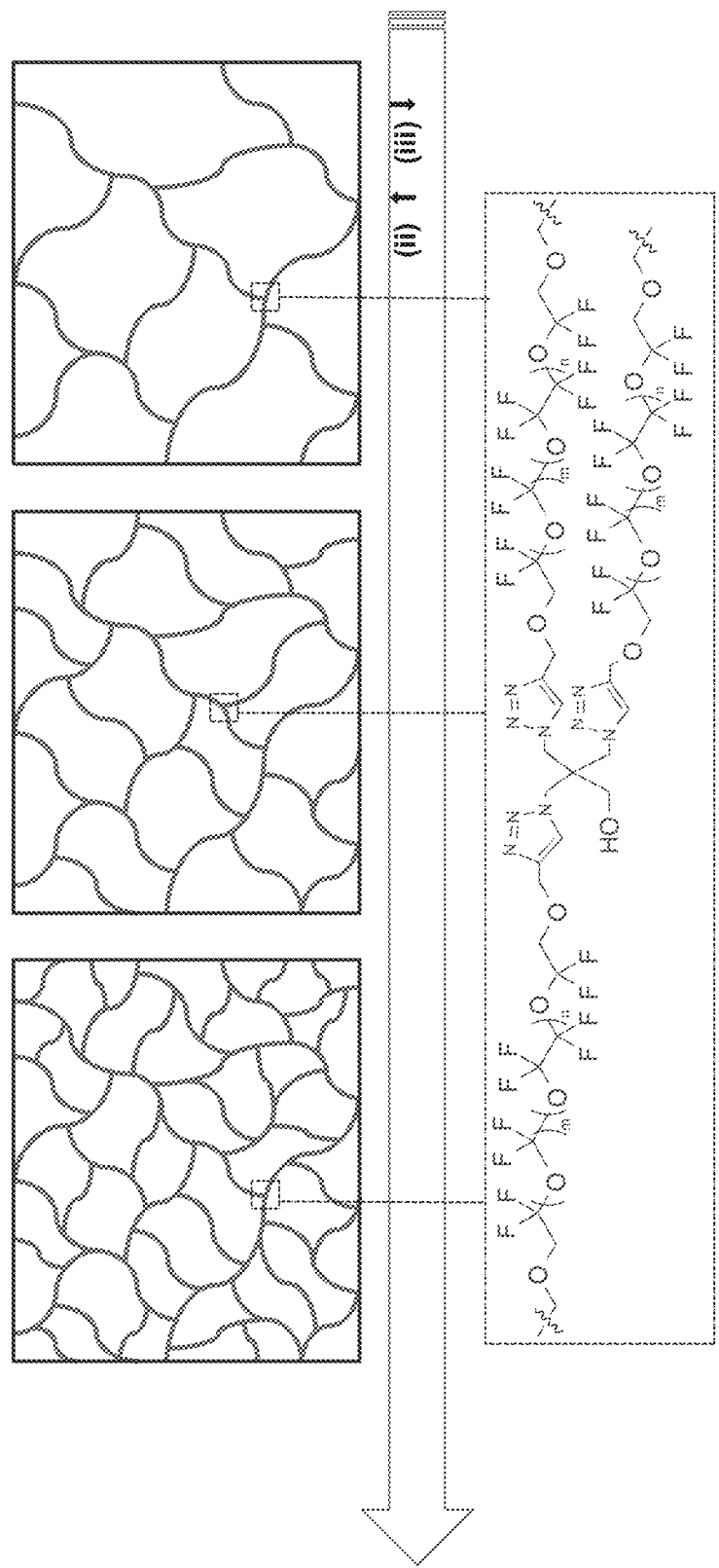

FIG. 16 shows a schematic representation of the structural differences of the cross-linked materials according to the invention as a function of the proportion of cross-linking agent (ii) and of α,ω-bis(azide) oligomer (iii) in the starting cross-linkable composition. The arrow indicates the direction of an increasing proportion of cross-linking agent (ii). The structure of a cross-linking point is indicated beneath the arrow.

Figure 17:
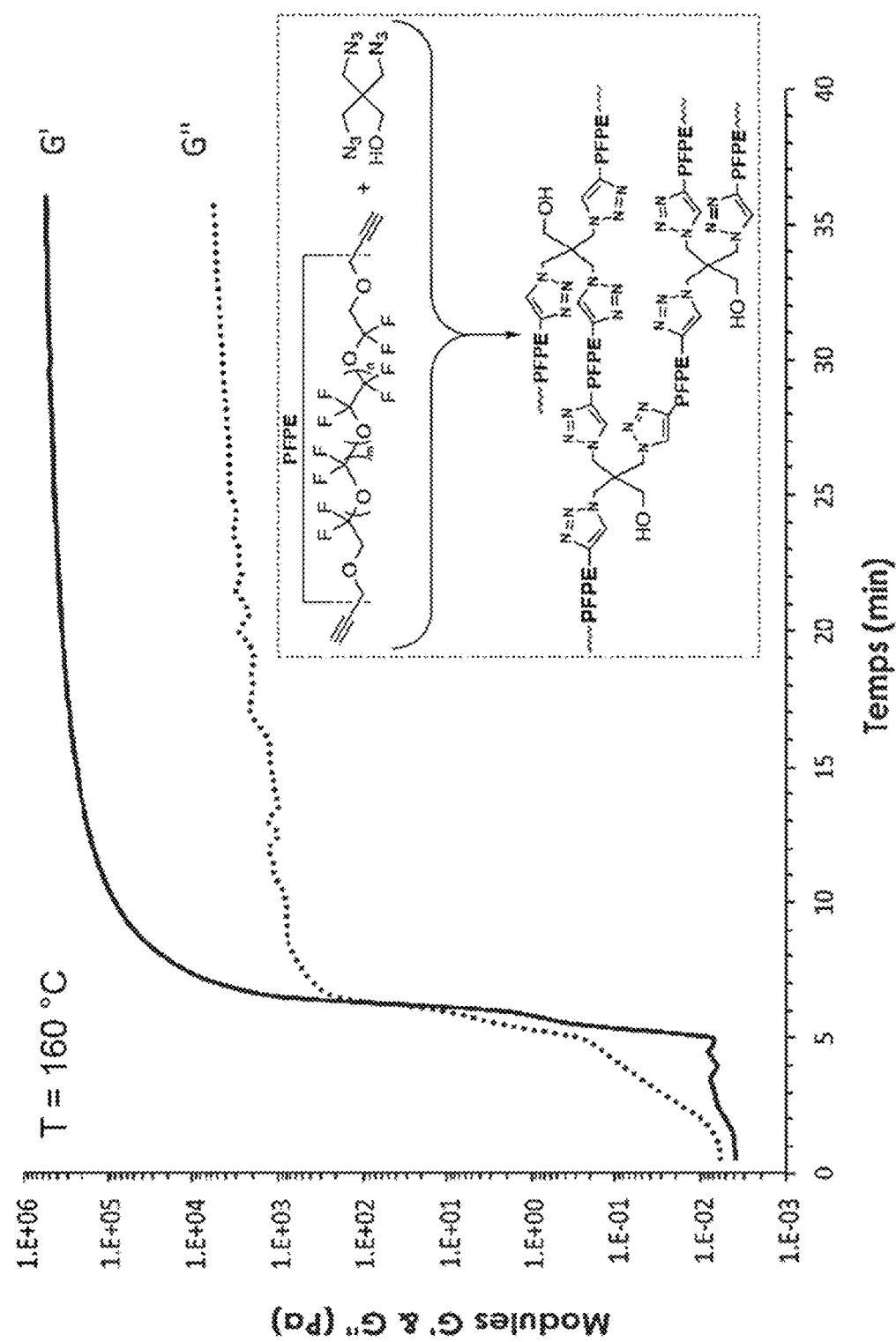

FIG. 17 describes the kinetic change (160° C.) in the viscoelastic moduli of the binary reactive formulation (i)+(ii) in a 3.2 molar ratio. The x-axis represents time (in min), and the y-axis represents moduli G' and G" (in Pa).

Figure 18:
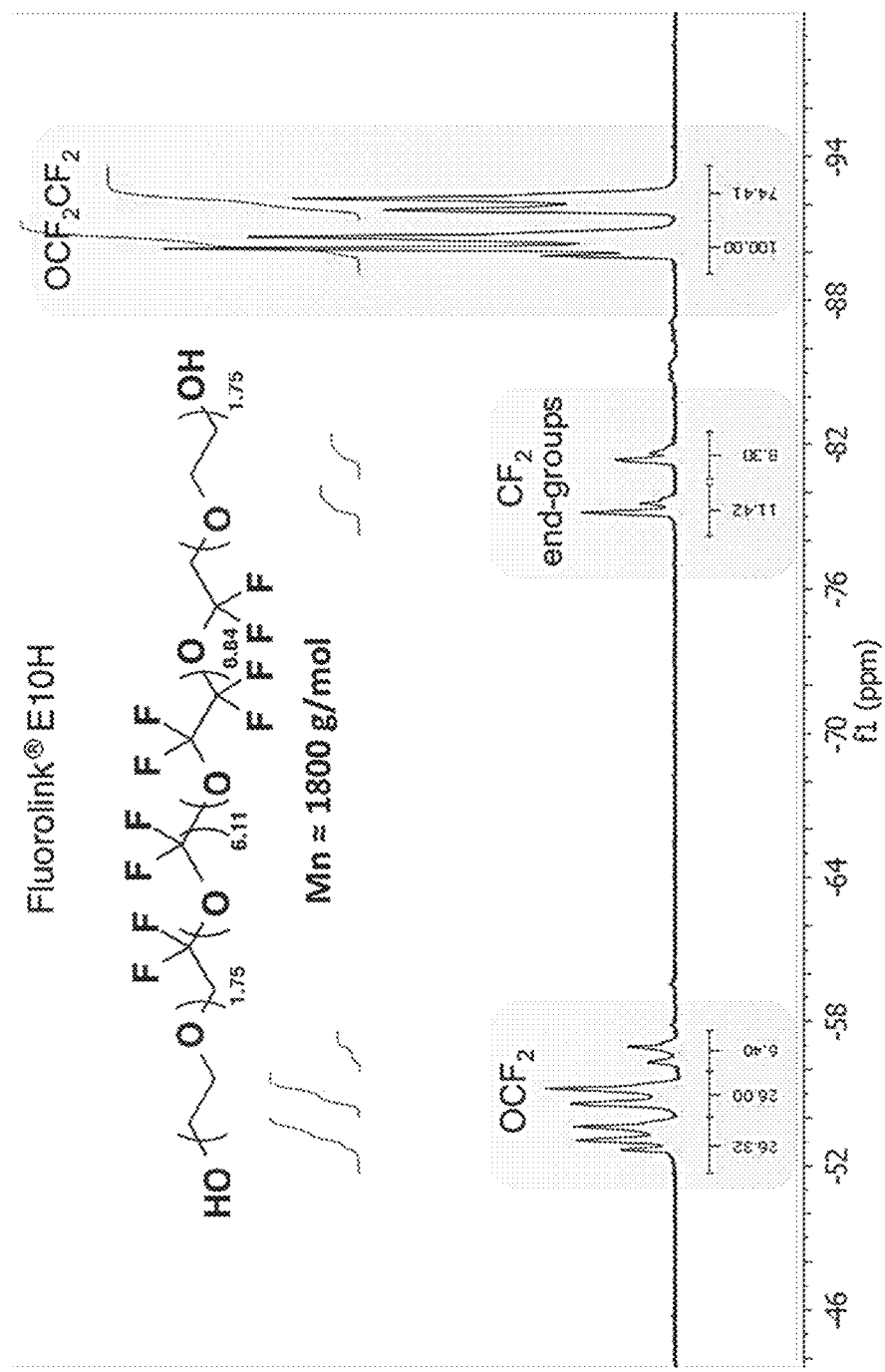

FIG. 18 shows the $^{19}$F NMR spectrum in deuterated acetone ((CH$_3$)$_2$CO-d$_6$) of Fluorolink® E10H. The x-axis represents chemical shifts in ppm.

Figure 19:
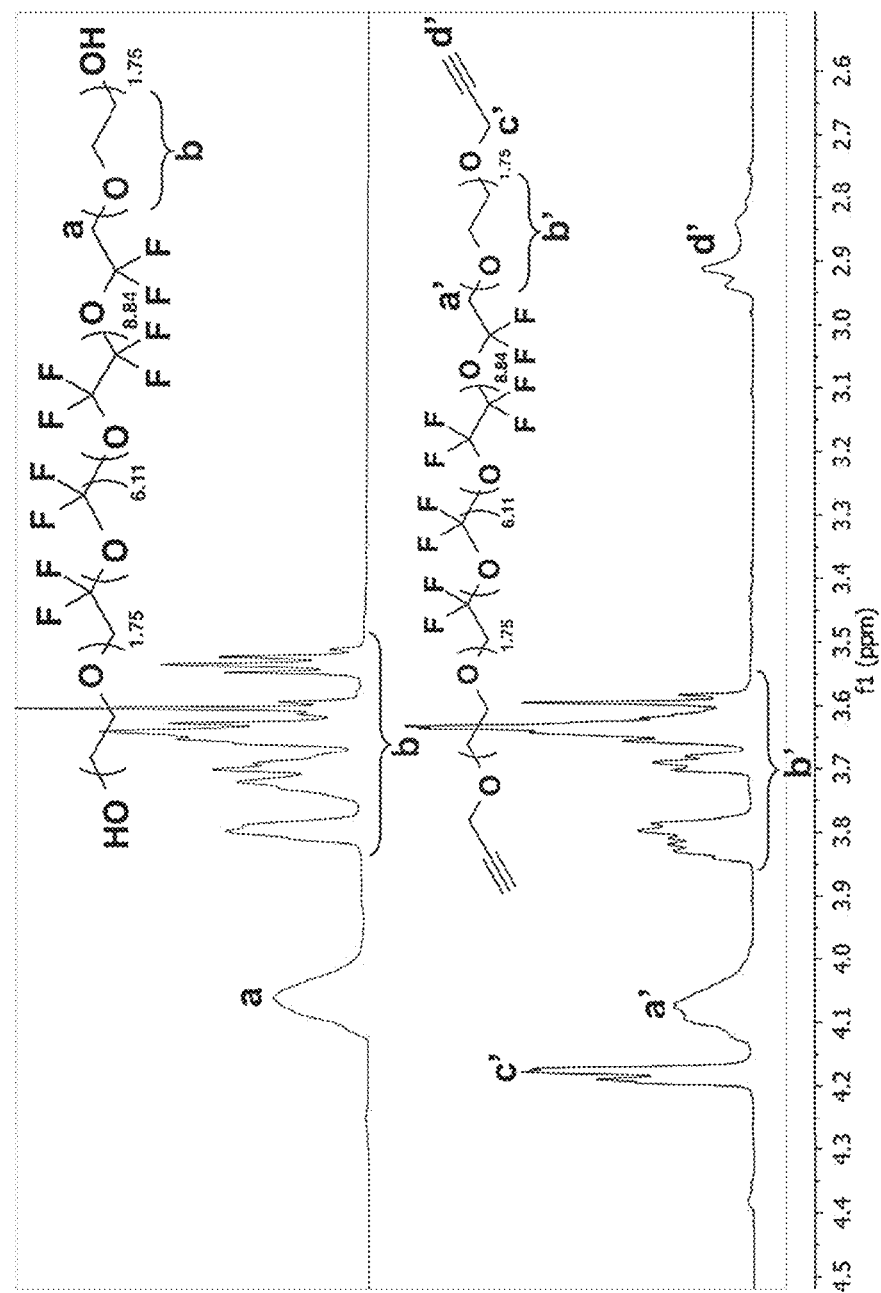

FIG. 19 shows a superposition of the $^1$H NMR spectra in deuterated acetone ((CH$_3$)$_2$CO-d$_6$) of Fluorolink® E10H and of the PFPE-dialkyne ether A' of Example 3. The x-axis represents chemical shifts in ppm.

Figure 20:
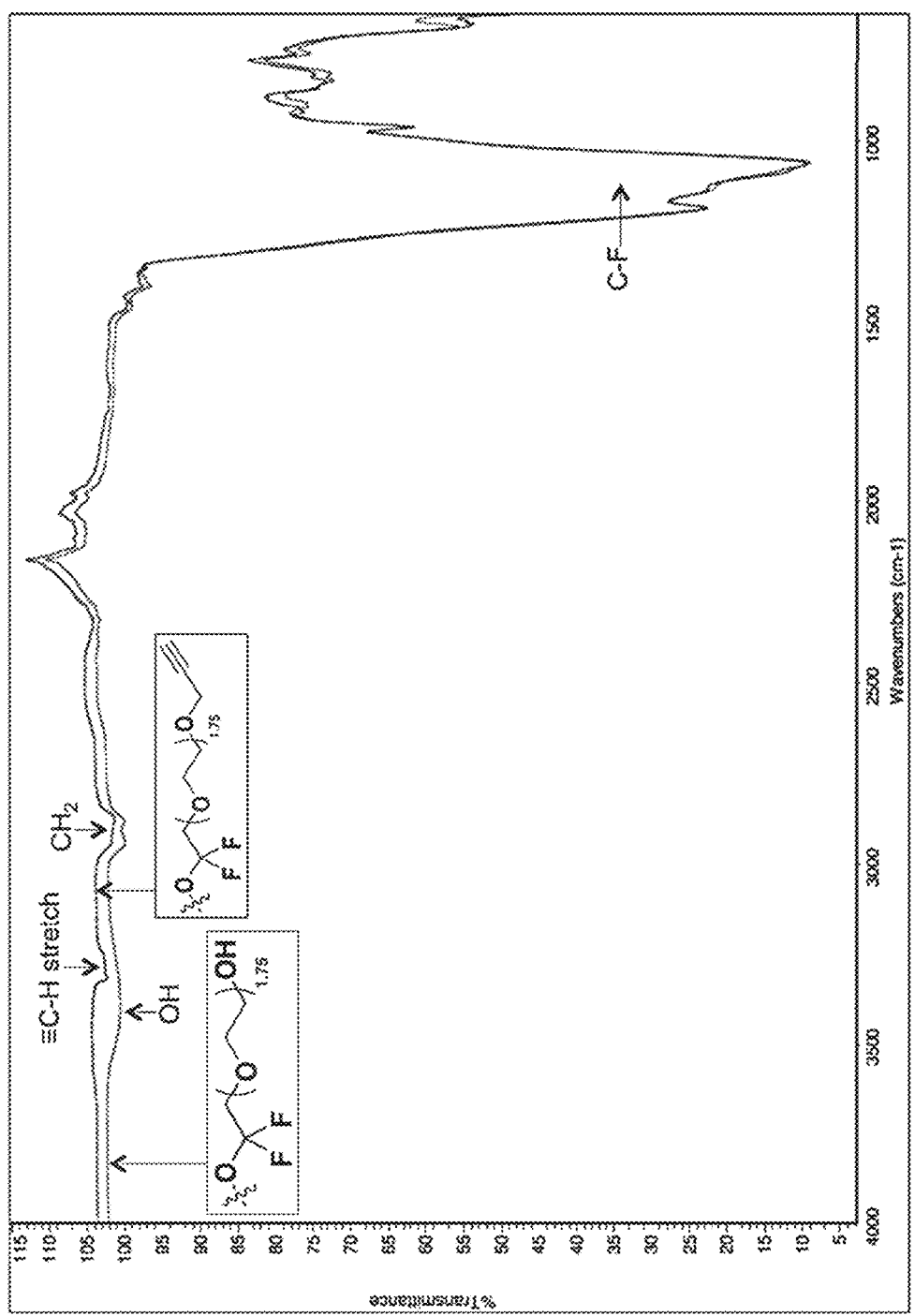

FIG. 20 shows a superposition of the FTIR spectra of Fluorolink® E10H and of the PFPE-dialkyne ether A' of Example 3. The x-axis represents wavenumber (in cm$^{-1}$), and the y-axis represents transmittance (in %).

Figure 21:
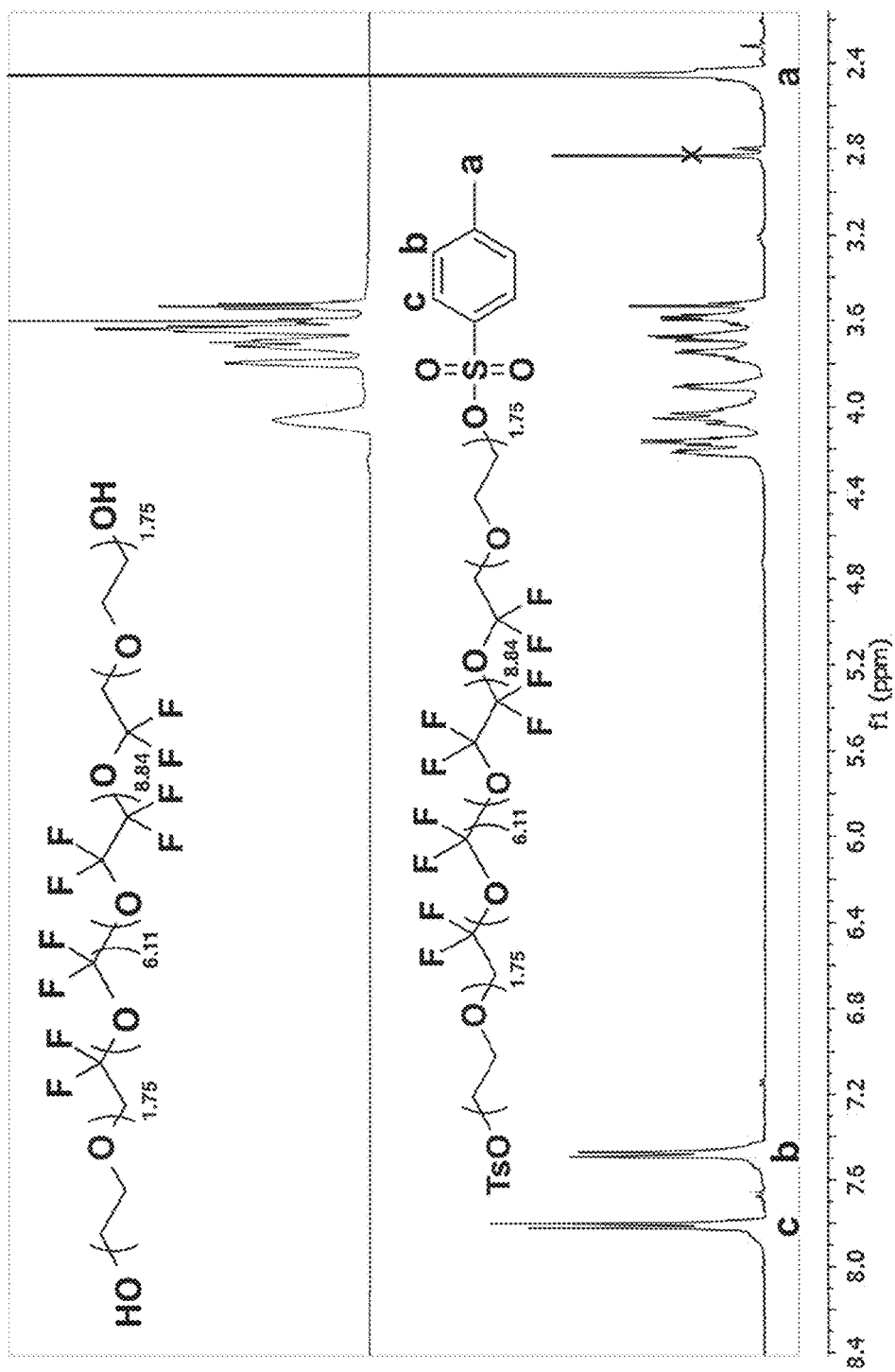

FIG. 21 shows a superposition of the $^1$H NMR spectra in deuterated acetone ((CH$_3$)$_2$CO-d$_6$) of Fluorolink® E10H and of the α,ω-bis(tosylate) PFPE of step 1 of Example 4. The x-axis represents chemical shifts in ppm.

Figure 22:
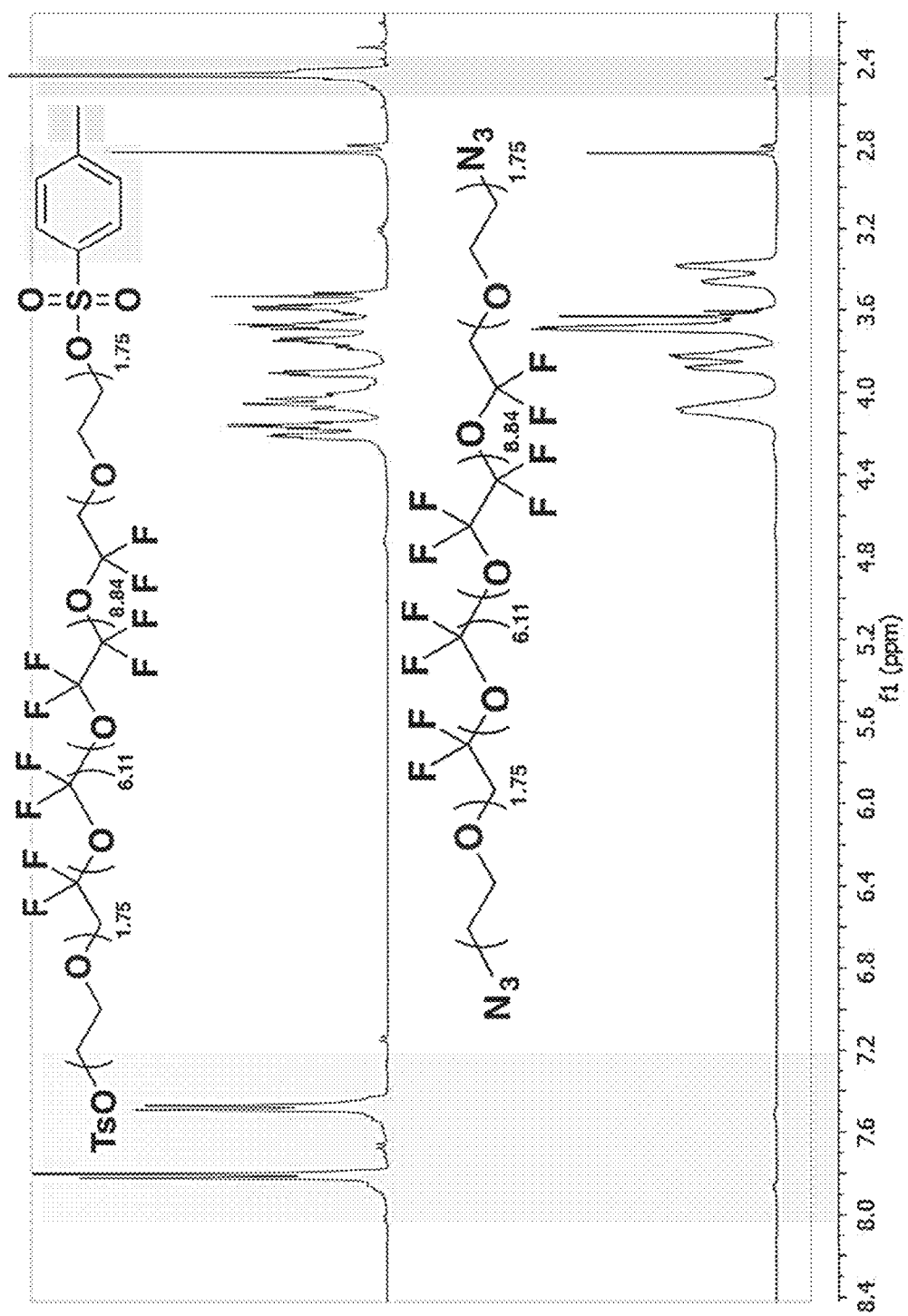

FIG. 22 shows a superposition of the $^1$H NMR spectra in deuterated acetone ((CH$_3$)$_2$CO-d$_6$) of the α,ω-bis(tosylate) PFPE of step 1 of Example 4 and of the α,ω-bis(azido) PFPE B' of step 2 of Example 4. The x-axis represents chemical shifts in ppm.

Figure 23:
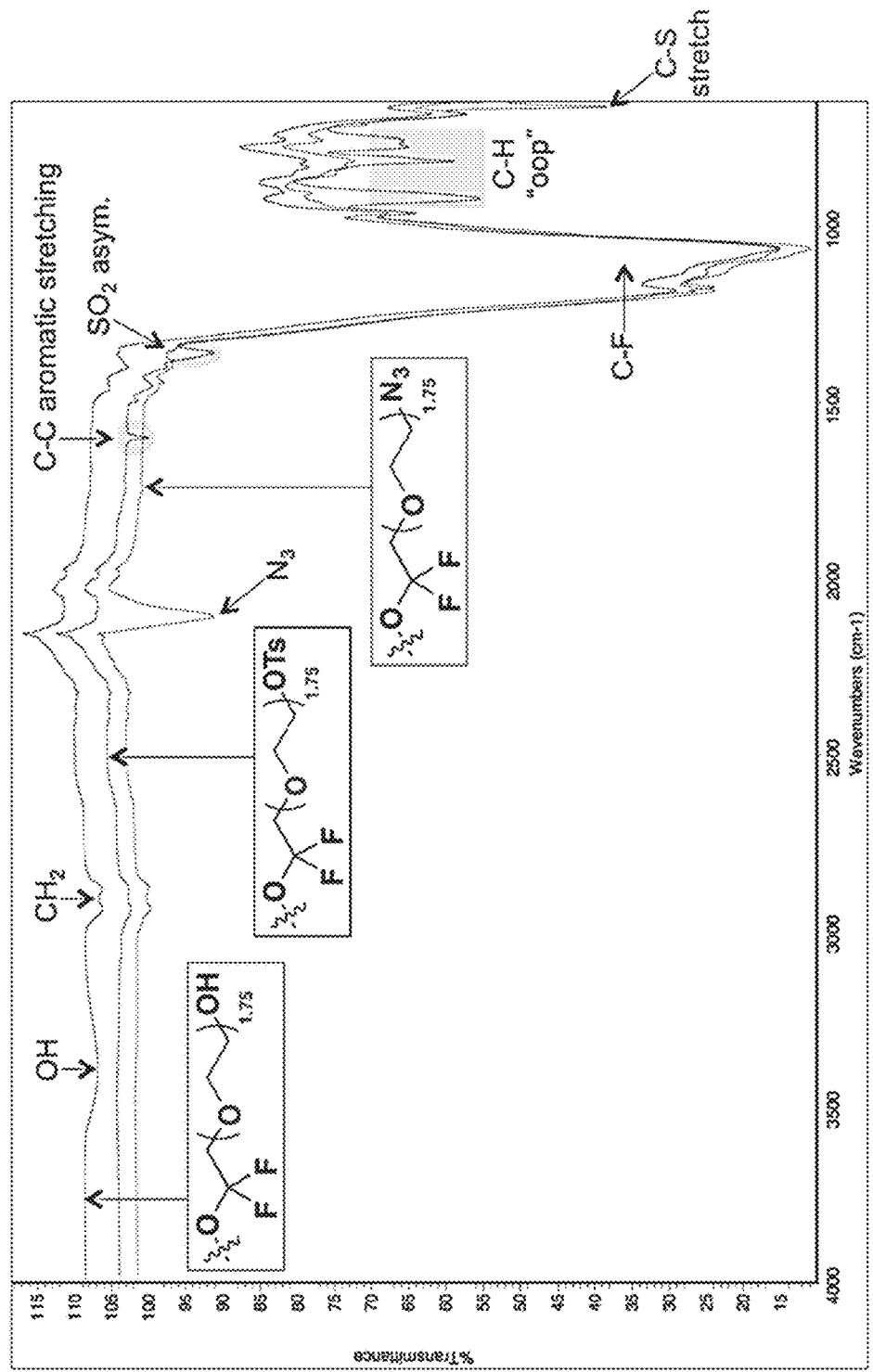

FIG. 23 shows a superposition of the FTIR spectra of Fluorolink® E10H, of the α,ω-bis(tosylate) PFPE of step 1 of Example 4, and of the α,ω-bis(azido) PFPE B' of step 1 of Example 4. The x-axis represents wavenumber (in cm$^{-1}$), and the y-axis represents transmittance (in %).

Figure 24:
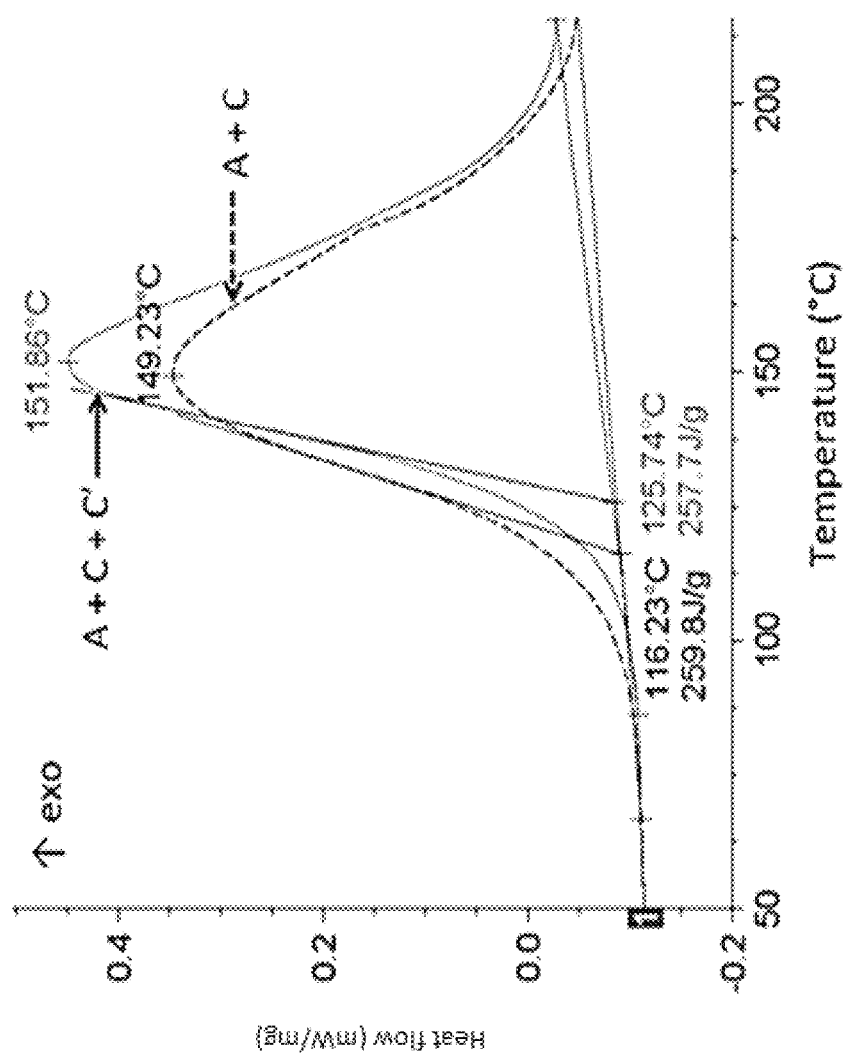

FIG. 24 shows the differential scanning calorimetry (DSC) analysis thermograms of mixtures A+C (1:0.67, mol/mol) and A+C+C' (1:0.603:0.067). The enthalpy of cross-linking is given in J/g. The x-axis represents temperature (in ° C.), and the y-axis represents heat flow (in mW/mg). Solid line: mixture A+C+C'; dotted line: mixture A+C.

EXAMPLES

The present invention is illustrated by the following examples, which may not however be regarded as limiting.

| | Abbreviations: |
|---|---|
| Eq. | Molar equivalent |
| NMR | Nuclear magnetic resonance |
| IR | Infrared |
| FTIR | Fourier-transform infrared |
| DMSO | Dimethylsulfoxide |
| DMF | Dimethylformamide |
| DSC | Differential scanning calorimetry |
| TGA | Thermogravimetric analysis |

Example 1: Synthesis of PFPE-Dialkyne Ether (Oligomer A)

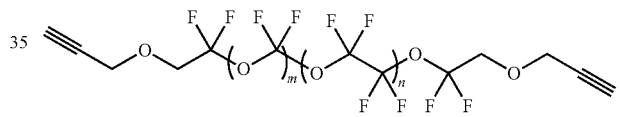

Figure 1:
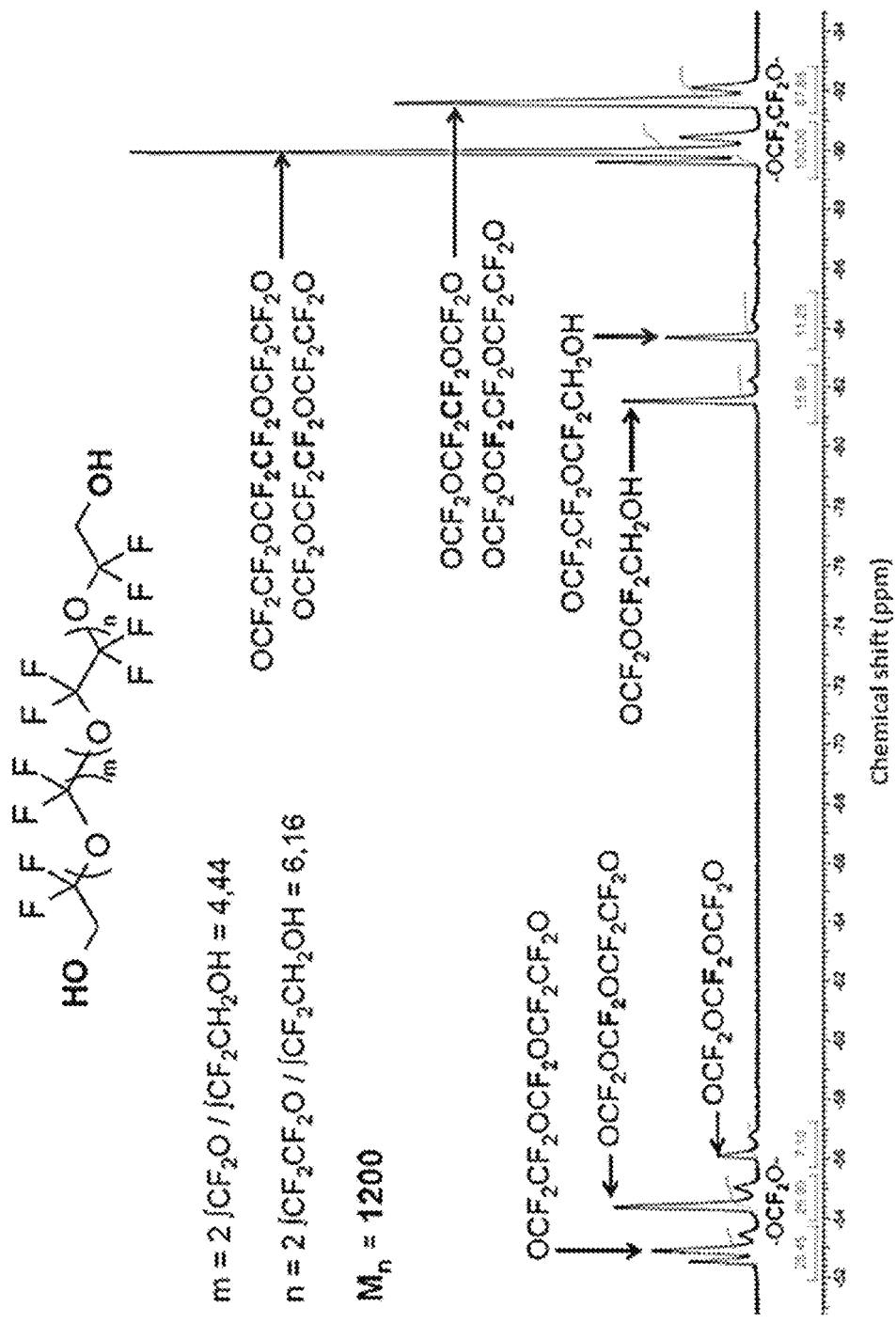
FIG. 1 shows the $^{19}F$ NMR spectrum in deuterated methanol (MeOH-$d_4$) of poly(tetrafluoroethylene oxide-co-difluoromethylene oxide)-α,ω-diol (Fomblin® Z-DOL), and the calculation of the number-average molar mass ($M_n$) (1200 g/mol). The x-axis represents chemical shifts in ppm.

Poly(tetrafluoroethylene oxide-co-difluoromethylene oxide)-α,ω-diol (Fomblin® Z-DOL, M$_n$ 1200 g/mol (FIG. 1), 20 g, 16.7 mmol, 1 eq.) is added to a mixture of CH$_3$CN (80 mL) and THF (80 mL), also containing sodium hydroxide (3.2 g, 83.5 mmol, 5 eq.). This suspension is heated to 55° C. under nitrogen atmosphere. Propargyl bromide (80 wt % solution in toluene, 10 mL, 83.5 mmol, 5 eq.) is added to the reaction mixture. The latter is heated to 55° C. under vigorous stirring for 3 days (>250 rpm). The reaction mixture is then cooled, filtered over a medium frit and the solvent is evaporated. The crude product is dried under vacuum (90·10$^{-3}$ mbar) and then purified by filtration through a 0.22 mm polyethersulfone filter, 17.5 g (82%) of light brown viscous oil is obtained.

Figure 2:
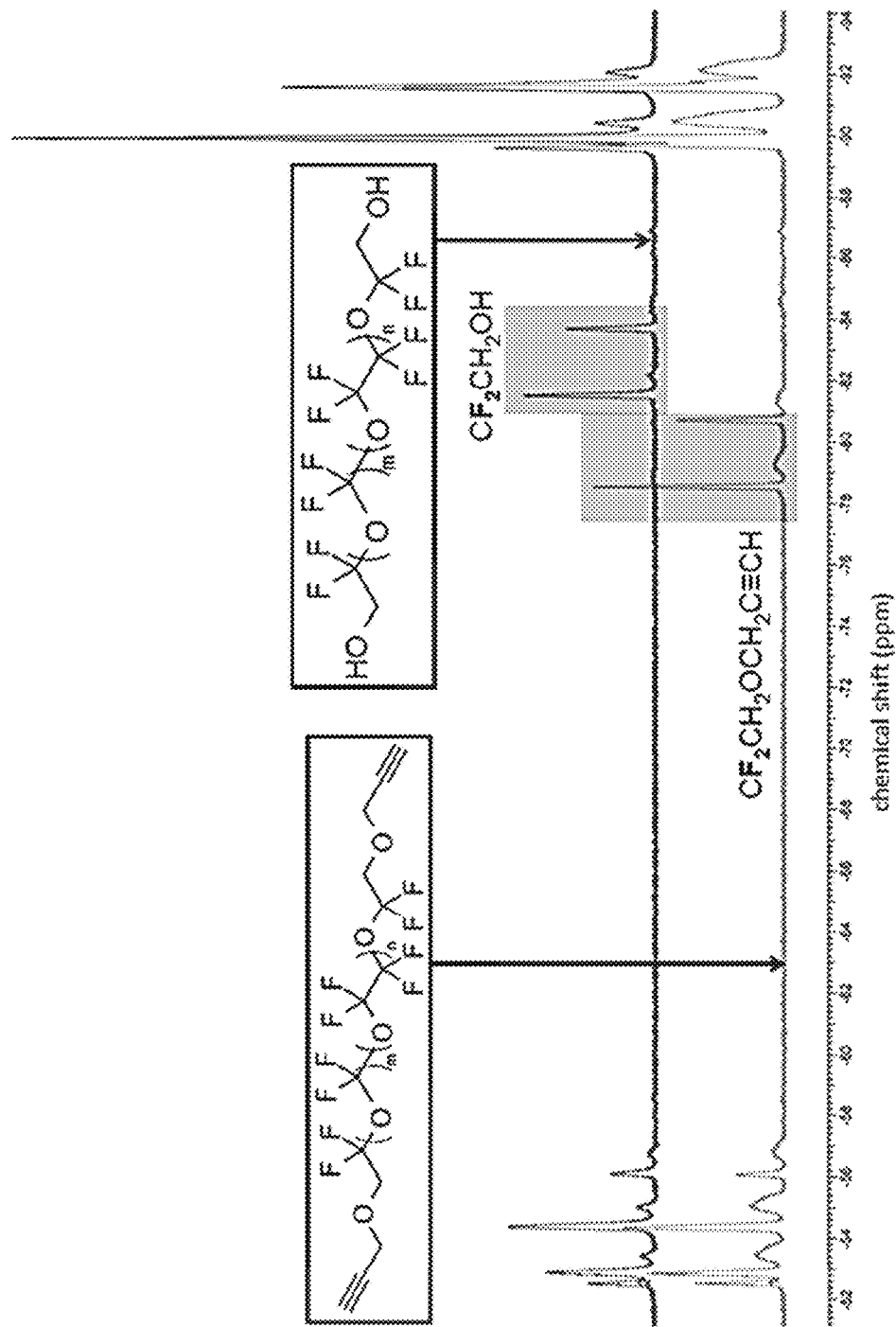
FIG. 2 shows a superposition of the $^{19}F$ NMR spectra in deuterated methanol (MeOH-$d_4$) of poly(tetrafluoroethylene oxide-co-difluoromethylene oxide)-α,ω-diol (Fomblin® Z-DOL) and of the PFPE-dialkyne ether of Example 1. The x-axis represents chemical shifts in ppm.
Figure 3:
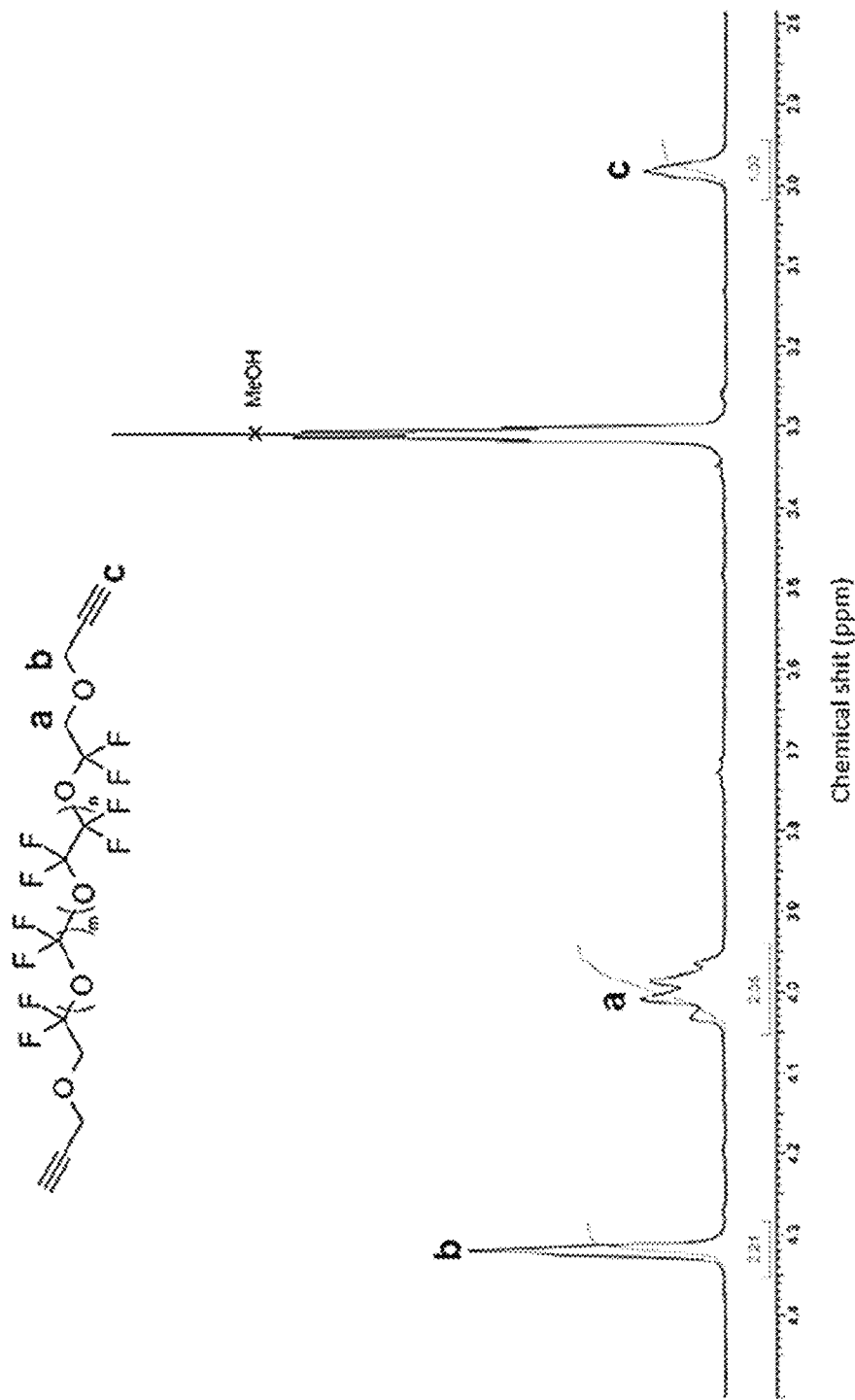
FIG. 3 shows the $^1H$ NMR spectrum in deuterated methanol (MeOH-$d_4$) of the PFPE-dialkyne ether of Example 1. The x-axis represents chemical shifts in ppm.
Figure 4:
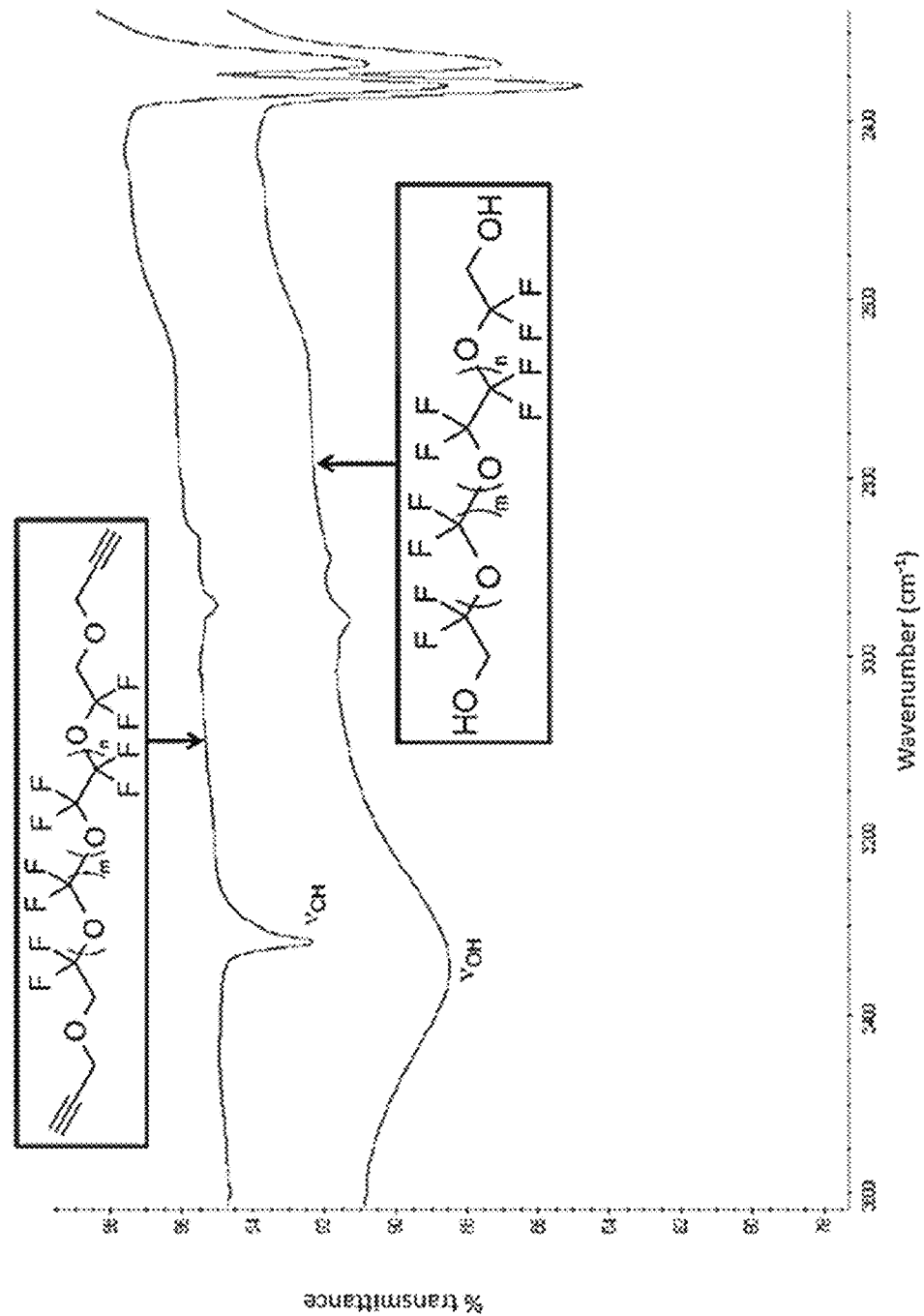
FIG. 4 shows a superposition of the infrared (FTIR) spectra of poly(tetrafluoroethylene oxide-co-difluoromethylene oxide)-α,ω-diol (Fomblin® Z-DOL) and of the PFPE-dialkyne ether of Example 1. The x-axis represents wavenumber (in $cm^{-1}$), and the y-axis represents transmittance (in %).

The $^{19}$F and $^1$H NMR spectra are shown in FIG. 2 and FIG. 3, respectively, and the FTIR spectrum in FIG. 4.

Example 2: Synthesis of α,ω-bis(azido) PFPE (Oligomer B)

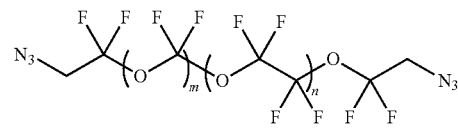

Step 1. Synthesis of α,ω-bis(tosylate) PFPE

Figure 8:
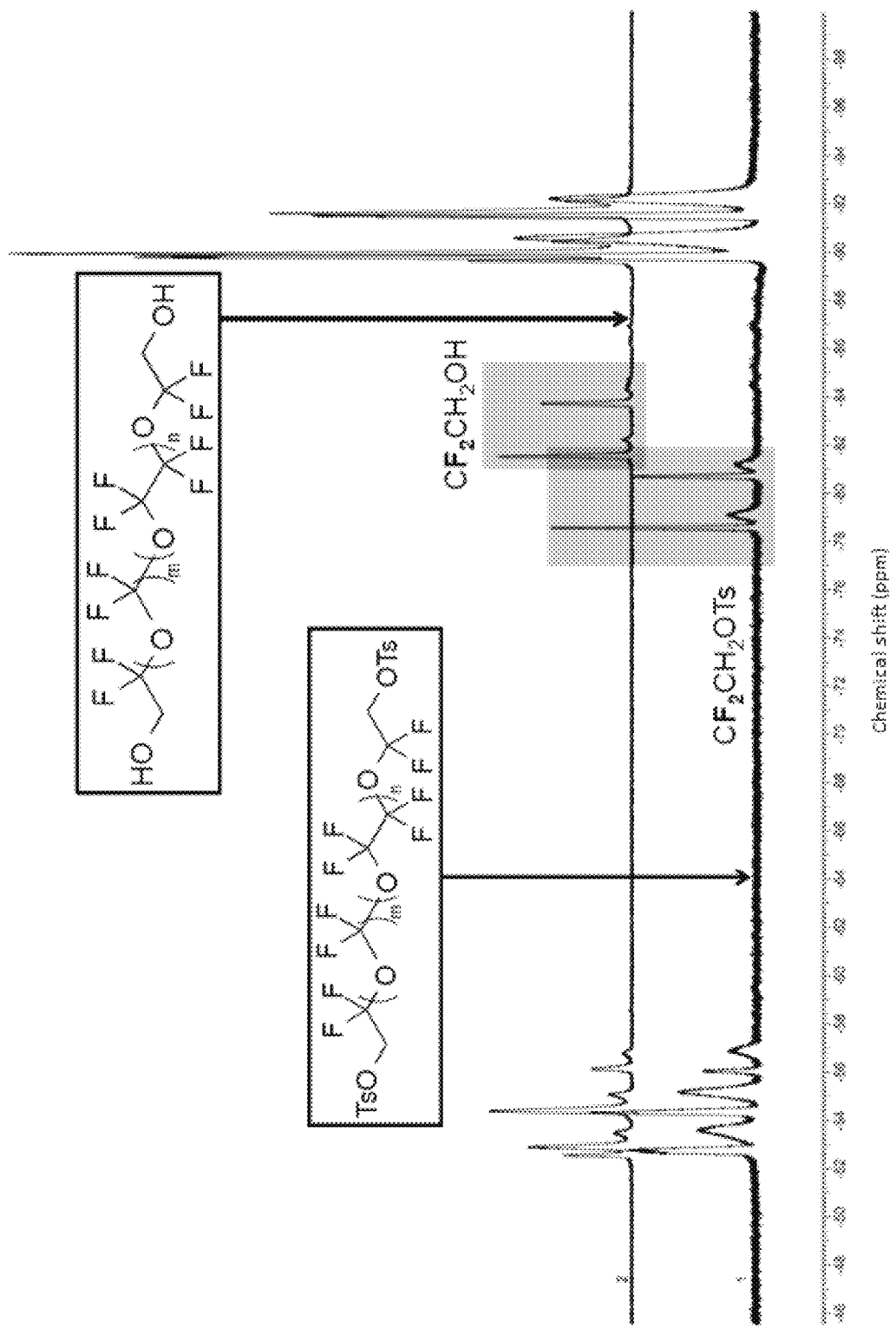
FIG. 8 shows a superposition of the $^{19}F$ NMR spectra in deuterated methanol (MeOH-$d_4$) of poly(tetrafluoroethylene oxide-co-difluoromethylene oxide)-α,ω-diol (Fomblin® Z-DOL) and of the α,ω-bis(tosylate) PFPE of step 1 of Example 2. The x-axis represents chemical shifts in ppm.
Figure 9:
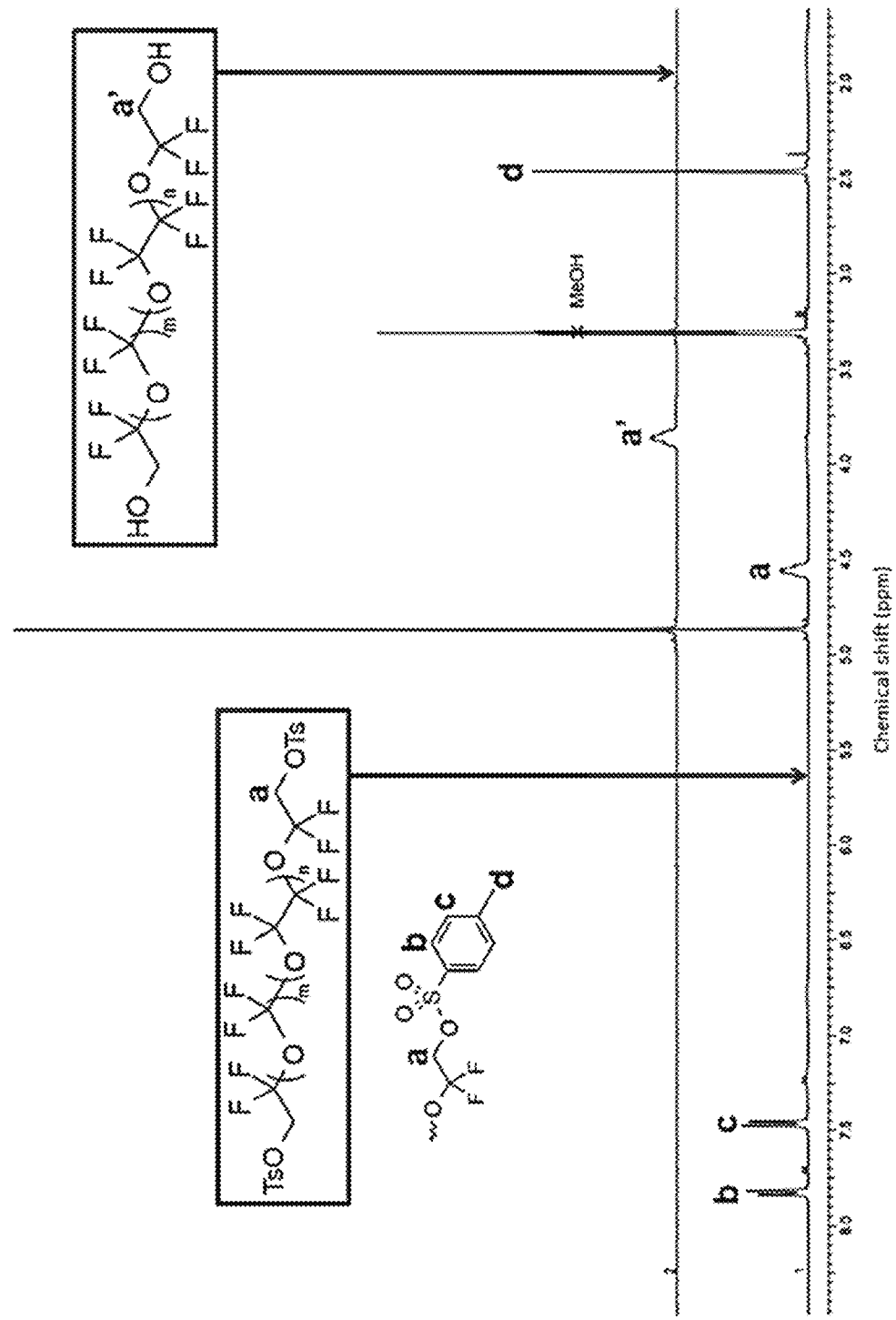
FIG. 9 shows a superposition of the $^1H$ NMR spectra in deuterated methanol (MeOH-$d_4$) of poly(tetrafluoroethylene oxide-co-difluoromethylene oxide) α,ω-diol (Fomblin®

Poly(tetrafluoroethylene oxide-co-difluoromethylene oxide)-α,ω-diol (Fomblin® Z-DOL, $M_n$ 1200 g/mol, 1 g, 0.83 mmol, 1 eq.) is dissolved in a mixture of α,α,α-trifluorotoluene (10 mL) and triethylamine (210 mg, 2 mmol, 2.5 eq.). Tosyl chloride (400 mg, 2 mmol, 2.5 eq.) is added to the reaction mixture, which is heated to 55° C. under vigorous stirring for 24 hours. Next, 10 mL of water and 1 mL of MeOH are added to the reaction mixture. The hydroalcoolic phase is removed, and the crude product is dried under reduced pressure (90·10⁻³ mbar) at 100° C. 1.15 g (92%) of light brown oil is obtained. The $^{19}$F and $^1$H NMR spectra are shown in FIG. 8 and FIG. 9, respectively, and the infrared (FTIR) spectrum in FIG. 12.

Step 2. Synthesis of α,ω-bis(azido) PFPE

A mixture of α,ω-bis(tosylate) PFPE (1 g, 0.66 mmol, 1 eq.), NaN₃ (260 mg, 3.98 mmol, 6 eq.), and DMSO (20 mL) is stirred at 110° C. for 3 days. The reaction mixture is then poured into water (100 mL), and then extracted with 1,1,1,3,3-pentafluorobutane (3×50 mL). The organic phases are combined, washed with water (3×50 mL), dried (MgSO₄), filtered and concentrated under vacuum. 770 mg (93%) of light brown oil is obtained.

The $^{19}$F NMR and $^1$H spectra are shown in FIG. 10 and FIG. 11, respectively, and the infrared (FTIR) spectrum in FIG. 12.

Example 3: Synthesis of PFPE-Dialkyne Ether (Oligomer A')

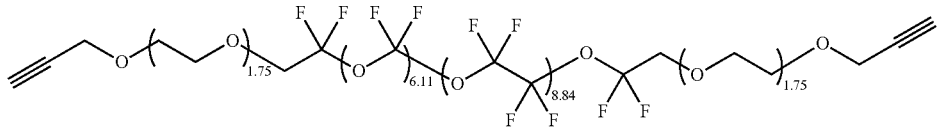

Fluorolink® E10H (FIG. 19, 1800 g/mol, 100 g, 55.6 mmol, 1 eq.) is added to a mixture of CH₃CN (150 mL) and THF (150 mL), also containing sodium hydroxide (16 g, 400 mmol, 7.2 eq.). This suspension is heated to 55° C. under nitrogen atmosphere. Propargyl bromide (80 wt % solution in toluene, 50 mL, 449 mmol, 8.1 eq.) is added to the reaction mixture. The latter is heated to 55° C. under vigorous stirring (>250 rpm) for 7 days. The reaction mixture is then cooled, filtered under vacuum and the solvent is evaporated. The crude product is dried under vacuum (20·10⁻³ mbar) at 100° C. and then purified by filtration through a 0.45 μm PTFE filter. 86 g (about 85%) of light brown oil is obtained. The $^1$H NMR spectrum is presented in FIG. 19, and the FTIR spectrum in FIG. 20. Differential scanning calorimetry analysis revealed a glass-transition temperature of −100° C.

Example 4: Synthesis of α,ω-bis(azido) PFPE (Oligomer B')

Step 1. Synthesis of α,ω-bis(tosylate) PFPE

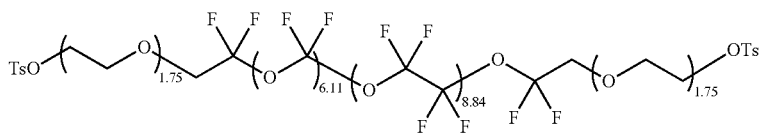

Fluorolink® E10H (1800 g/mol, 100 g, 55.6 mmol, 1 eq.) is dissolved in a mixture of 1,1,1,3,3-pentafluorobutane (300 mL) and triethylamine (28 g, 277 mmol, 5 eq.). Tosyl chloride (53 g, 278 mmol, 5 eq.) is added to the reaction mixture, which is heated to 30° C. under vigorous stirring for 7 days. The fluorinated phase is then washed with water (3×300 mL), dried over MgSO$_4$, filtered, and then evaporated under reduced pressure. The crude product is then dried under reduced pressure (20·10$^{-3}$ mbar) at 100° C. 70 g (about 70%) of light brown oil is obtained. The $^1$H NMR spectrum is presented in FIG. 21, and the FTIR spectrum in FIG. 23.

Step 2. Synthesis of α,ω-bis(azido) PFPE B'

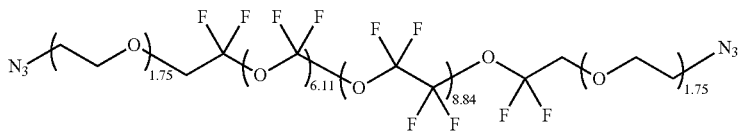

A mixture of α,ω-bis(tosylate) PFPE (70 g, 38.9 mmol, 1 eq.) synthesized during the first step, NaN$_3$ (27 g, 415 mmol, 10.7 eq.), and DMSO (300 mL) is stirred at 100° C. for 7 days. The reaction mixture is then poured into water (300 mL), and then extracted with 1,1,1,3,3-pentafluorobutane (3×150 mL). The organic phases are combined, washed with water (3×150 mL), dried (MgSO$_4$), filtered and concentrated under vacuum. The crude product is then dried under reduced pressure (20·10$^{-3}$ mbar) at 100° C., 42 g (about 60%) of light brown oil is obtained. The $^1$H NMR spectrum is presented in FIG. 22, and the FTIR spectrum in FIG. 23. Differential scanning calorimetry analysis revealed a glass-transition temperature of −105° C. and a degradation temperature of about 180° C.

Example 5: Synthesis of Pentaerythritol Triazide (Cross-Linking Agent C)

This synthesis employs as starting compound 3-bromo-2,2-bis(bromomethyl)propanol (commercial product available for example from ABCR), according to a protocol described notably in Dalton Trans. 2012, 41, 4335; Biomaterials 2014, 35, 2322: Chem. Commun. 2007, 380; WO2012131278.

A mixture of 3-bromo-2,2-bis(bromomethyl)propanal (10 g, 31 mmol, 1 eq.), NaN$_3$ (12 g, 186 mmol, 6 eq.), and DMSO (30 mL) is mixed at 100° C. for 2 days. The reaction mixture is then poured into water (200 mL) and then extracted with chloroform (CHCl$_3$; 3×100 mL). The organic phases are combined and then washed with water (3×100 mL), dried (MgSO$_4$), filtered and concentrated under reduced pressure to give 5.70 g (87%) of pale yellow oil.

$^1$H NMR (CDCl$_3$), δ (ppm): 2.20 (br. s, 1H, —OH); 3.36 (s, 6H, —CH$_2$—N$_3$); 3.52 (s, 2H, —CH$_2$—OH).

FTIR-ATR: 2100 cm$^{-1}$ ($\nu_{N3}$); 3400 cm$^{-1}$ ($\nu_{OH}$).

Example 6: Phosphorus-Containing Cross-Linking Agent (Cross-Linking Agent C')

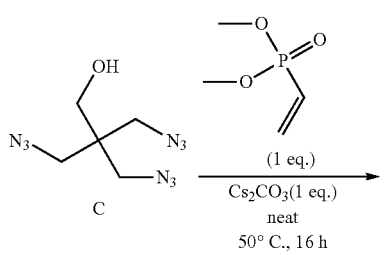

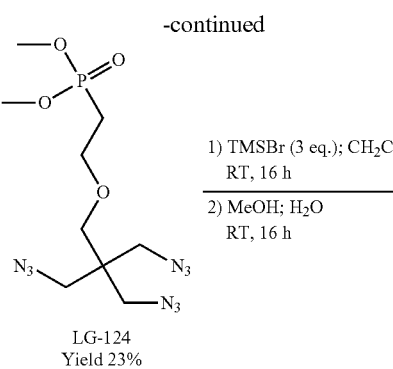

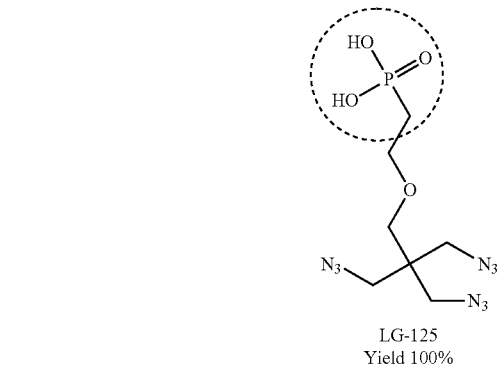

Pentaerythritol triazide (2 g, 9.47 mmol, 1 eq.) is heated for 16 hours at 50° C. in the presence of dimethyl vinyl-phosphonate (1.29 g, 9.47 mmol, 1 eq.) and cesium carbonate (3.08 g, 9.47 mmol, 1 eq.). The reaction medium is then diluted with water (100 mL) and then extracted with ethyl acetate (3×100 mL). The organic phases are combined, dried (MgSO$_4$), and then evaporated under reduced pressure. The residue is purified by silica-gel column chromatography (eluent: dichloromethane/ethyl acetate, 90:10) to give 760 mg (23%) of colorless oil.

$^1$H NMR (CDCl$_3$), δ (ppm): 2.09 (dt, 2H, P—CH$_2$, $^2J_{HP}$=18.6 Hz, $^3J_{HH}$=7.3 Hz); 3.28 (s, 2H, O—CH$_2$—C(CH$_2$N$_3$)$_3$; 3.32 (s, 6H, O—CH$_2$—C(CH$_2$N$_3$)$_3$; 3.68 (dt, 2H, P—CH$_2$—CH$_2$, $^3J_{HP}$=13.2 Hz, $^3J_{HH}$=7.3 Hz); 3.73 (d, 6H, CH$_3$O—, $^3J_{HP}$=10.9 Hz).

$^{13}$C NMR (CDCl$_3$), δ (ppm): 25.9 (d, P—CH$_2$, $^1J_{CP}$=140.4 Hz); 45.0 (C(CH$_2$N$_3$)$_3$); 51.2 (C(CH$_2$N$_3$)$_3$); 52.5 (d, CH$_3$O, $^2J_{CP}$=6.5 Hz); 65.3 (d, P—CH$_2$—CH$_2$, $^2J_{CP}$=1.8 Hz); 69.3 (O—CH$_2$—C(CH$_2$N$_3$)$_3$).

$^{31}$P NMR (CDCl$_3$), δ (ppm): 30.7

The latter is diluted in dichloromethane (10 mL) and then trimethylsilyl bromide (about 0.5 mL) is added dropwise. The reaction medium is left for 16 hours at room temperature before being concentrated under reduced pressure. The residue is then diluted with a methanol water mixture (10 mL/10 mL) for 16 hours at room temperature. After evaporation, a slightly yellow oil is obtained (420 mg, 100%).

$^1$H NMR (CDCl$_3$), δ (ppm): 2.15 (dt, 2H, P—CH$_2$, $^2J_{HP}$=16.5 Hz, $^3J_{HH}$=7.1 Hz); 3.27 (s, 2H, O—CH$_2$—C(CH$_2$N$_3$)$_3$; 3.29 (s, 6H, O—CH$_2$—C(CH$_2$N$_3$)$_3$; 3.72 (dt, 2H, P—CH$_2$—CH$_2$, $^3J_{HP}$=12.8 Hz, $^3J_{HH}$=7.1 Hz); 9.49 (br s, 1H, HO—).

$^{13}$C NMR (CDCl$_3$), δ (ppm): 26.5 (d, P—CH$_2$, $^1J_{CP}$=145.6 Hz); 44.7 (C(CH$_2$N$_3$)$_3$); 51.8 (C(CH$_2$N$_3$)$_3$); 65.0 (P—CH$_2$—CH$_2$); 69.6 (O—CH$_2$—C(CH$_2$N$_3$)$_3$).

$^{31}$P NMR (CDCl$_3$), δ (ppm): 32.5

Example 7: Cross-Linked Materials 7.1. Cross-Linking By Click Chemistry with PFPE-Dialkyne Ether and Pentaerythritol Triazide ("Binary" Material)

PFPE-dialkyne ether (4.55 g, 3.57 mmol, 1 eq.) and pentaerythritol triazide (810 mg, 3.83 mmol, 1.07 eq.) are suspended in DMF (20 mL). The mixture is degassed by nitrogen bubbling for 30 minutes. Next, CuBr (52 mg, 0.036 mmol, 0.1 eq.) and N,N,N',N'',N''-pentamethyldiethyenetriamine (PMDETA, 62 mg, 0.036 mmol, 0.1 eq.) are added to the reaction medium which instantaneously turns green. After stirring for 1 hour, the insoluble polymer is washed several times with a DMF:PMDETA mixture (20 mL:1 mL) until the rinse solution remains colorless. The polymer is then dried under vacuum at 100° C. until a constant weight is obtained (4.40 g, 82 wt %).

Figure 5:
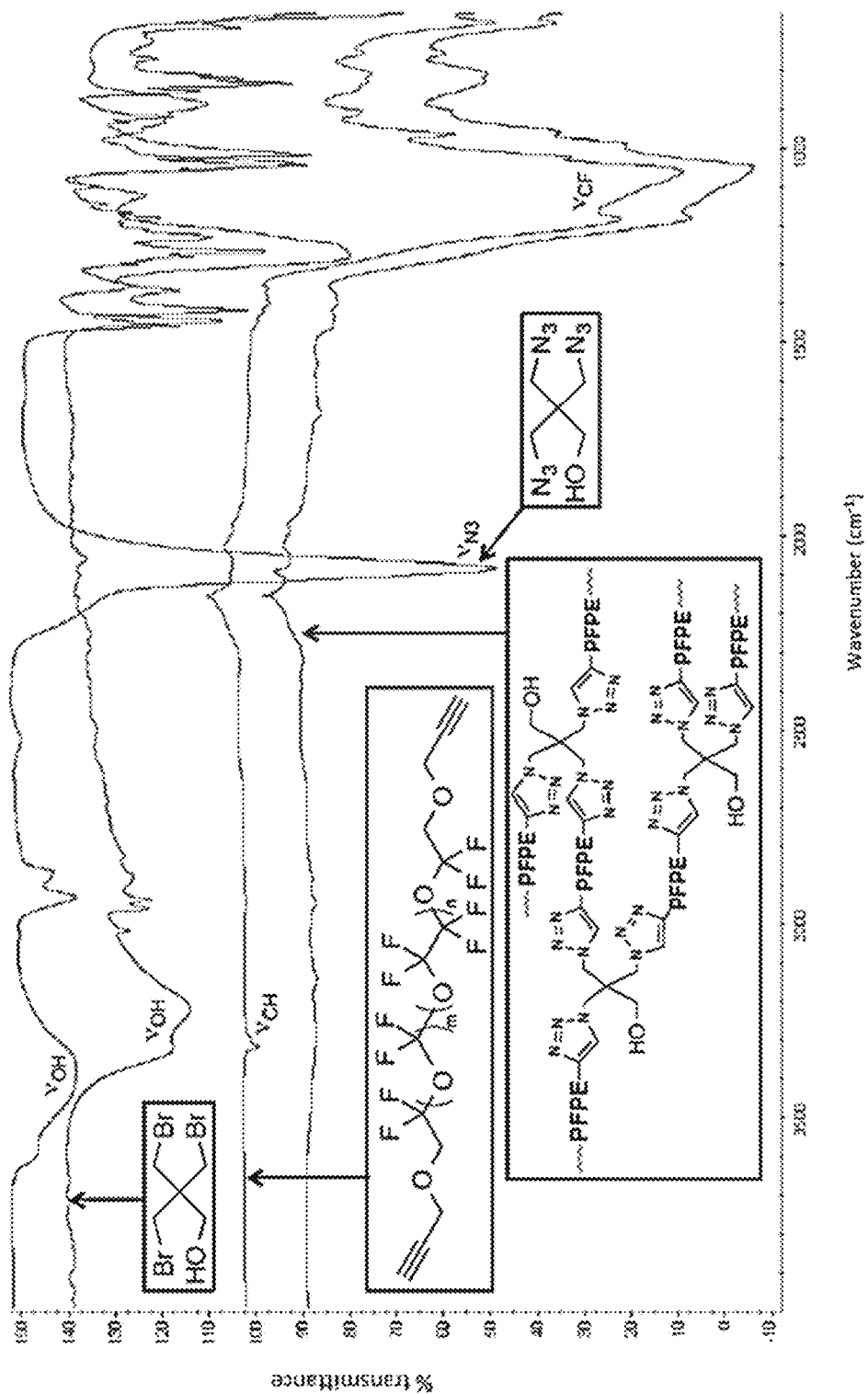
FIG. 5 shows a superposition of the Fourier-transform infrared (FTIR) spectra of the pentaerythritol triazide of Example 5, and of the PFPE-dialkyne ether of Example 1 and of the "binary" material of Example 7.1, and the IR spectrum of the tribrominated precursor compound of pentaerythritol triazide. The x-axis represents wavenumber (in $cm^{-1}$), and the y-axis represents transmittance (in %).

The polymer is then analyzed by infrared spectroscopy (FTIR, FIG. 5).

Figure 6:
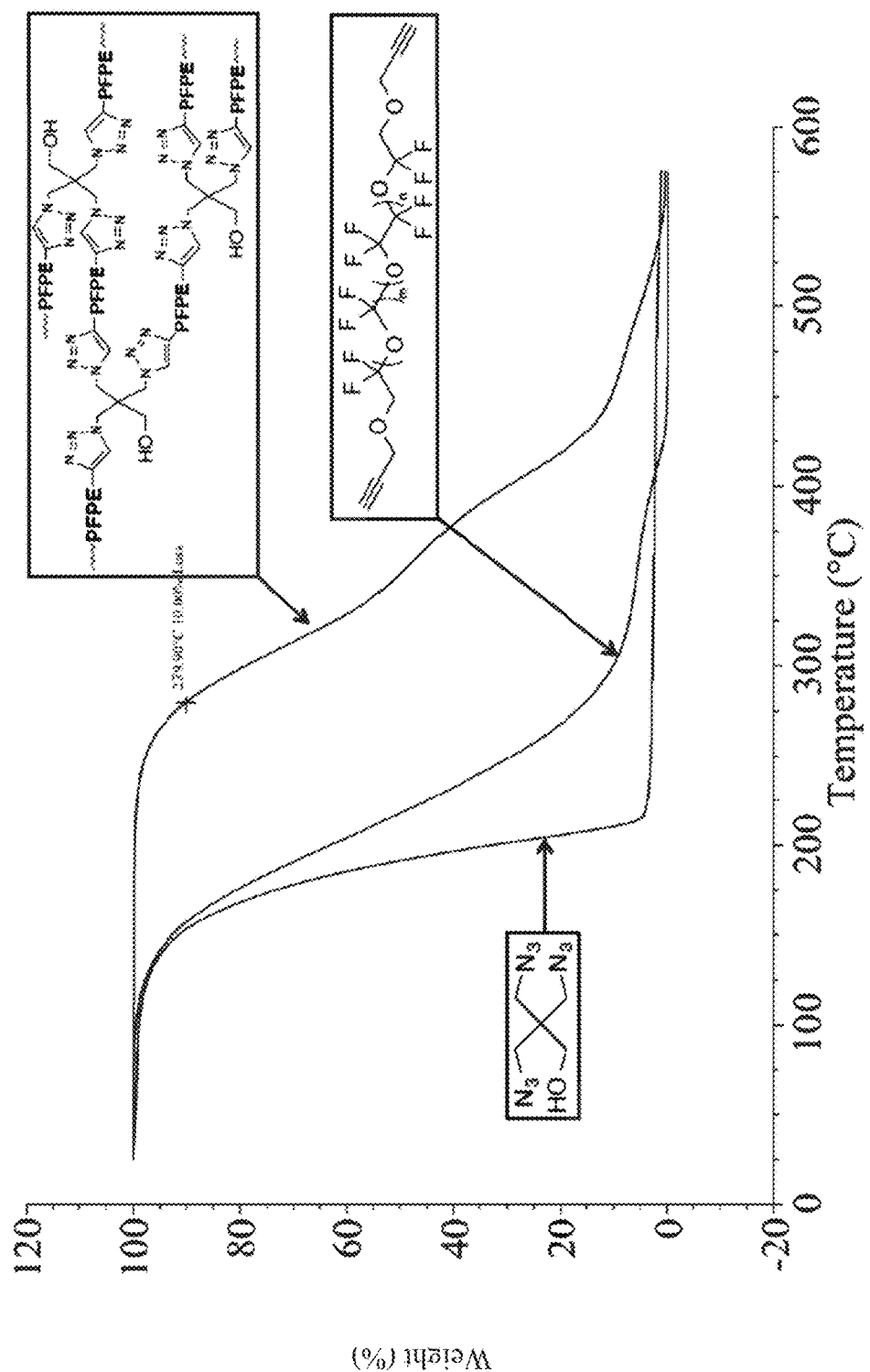
FIG. 6 shows a superposition of the thermogravimetric analysis (TGA) thermograms at 10° C. per minute in air, of the "binary" material of Example 7.1 and the precursors thereof, the pentaerythritol triazide of Example 5, and the PFPE-dialkyne ether of Example 1. The x-axis represents temperature (in ° C.), and the y-axis represents weight (in %).
Figure 7:
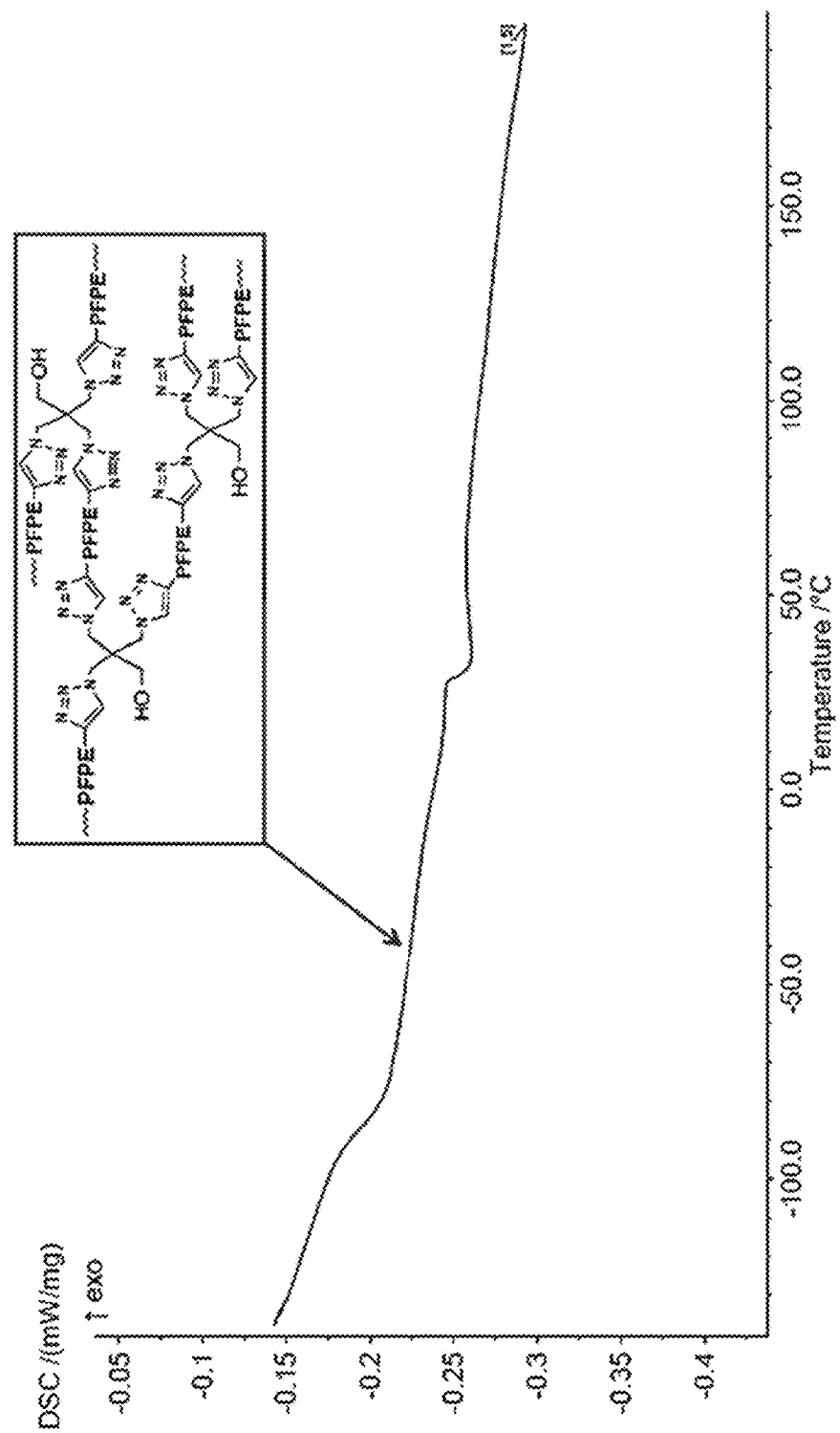
FIG. 7 shows the differential scanning calorimetry (DSC) analysis thermogram of the "binary" material of Example 7.1, The x-axis represents temperature (in ° C.), and the y-axis represents heat flow per unit mass (in mW/mg).

Thermogravimetric analysis (TGA) reveals a decomposition temperature at 10% weight loss ($T_d^{10\%}$) of 280° C., in air. (FIG. 6). Differential scanning calorimetry analysis reveals a glass-transition temperature ($T_g$) value at −87° C. (FIG. 7).

7.2. Click Cross-Linking with PFPE-Dialkyne Ether, α,ω-bis(azido) PFPE and Pentaerythritol Triazide ("Ternary" Material)

PFPE-dialkyne ether (472 mg, 0.37 mmol, 0.525 eq.), α,ω-bis(azido) PFPE (400 mg, 0.32 mmol, 0.450 eq.) and pentaerythritol triazide (10 mg, 0.04 mmol, 0.05 eq.) are suspended in DMF (20 mL). The mixture is degassed by nitrogen bubbling for 30 minutes. Next, CuBr (10 mg, 0.07 mmol, 0.1 eq.) and N,N,N',N'',N''-pentamethyldiethylenetriamine (PMDETA, 10 mg, 0.07 mmol, 0.1 eq.) are added to the reaction medium which instantaneously turns green. After stirring for 1 hour, the insoluble polymer is washed several times with a DMF:PMDETA mixture (20 mL:1 mL) until the rinse solution remains colorless. The polymer is then dried under vacuum at 100° C. until a constant weight is obtained (800 mg, 91 wt %).

Kinetic rheological analysis (FIG. 17) reveals that the gel point associated with critical production of the polymer network is detected by the divergence of the viscoelastic moduli. The associated gel time is about 6 minutes at a temperature of 160° C. whereas the reaction seems to have reached a maximum degree of advancement after 30 minutes. These values underscore that the mixture has a reactivity which is perfectly compatible with the productivity demands of an industrial process.

Thermogravimetric analysis (TGA) reveals a decomposition temperature at 10% weight loss ($T_d^{10\%}$) of 291° C. in air (FIG. 13). Differential scanning calorimetry analysis reveals a glass-transition temperature ($T_g$) value at −100° C. (FIG. 14).

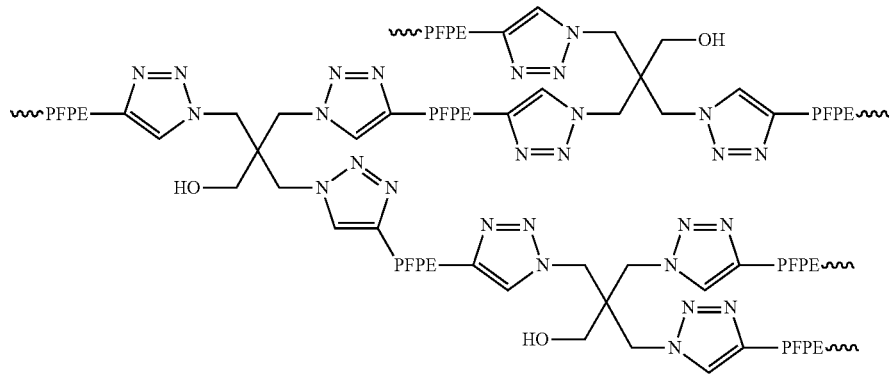

7.3. Ternary Formulations with Pentaerythritol Triazide of Examples 1 and 2: Variation of the Proportion of Cross-Linking Agent Four materials were prepared with variable ratios of α,ω-bis(azide) oligomers/cross-linking agent (here, pentaerythritol triazide) in the starting cross-linkable composition. They are designated as follows:

LG-75: material obtained by cross-linking of a cross-linkable composition within which 20% of the azide functions are provided by the cross-linking agent (i.e., the remaining 80% are provided by the α,ω-bis(azide) oligomer, α,ω-bis(azido) PFPE);

LG-76: material obtained by cross-linking of a cross-linkable composition within which 40% of the azide functions are provided by the cross-linking agent (i.e., the remaining 60% are provided by the α,ω-bis(azide) oligomer, α,ω-bis(azido) PFPE);

LG-77: material obtained by cross-linking of a cross-linkable composition within which 60% of the azide functions are provided by the cross-linking agent (i.e., the remaining 40% are provided by the α,ω-bis(azide) oligomer, α,ω-bis(azido) PFPE).

LG-78: material obtained by cross-linking of a cross-linkable composition within which 80% of the azide functions are provided by the cross-linking agent (i.e., the remaining 20% are provided by the α,ω-bis(azide) oligomer, α,ω-bis(azido) PFPE).

The comparative study of the calorimetric behavior of these four materials as a function of temperature is shown in FIG. 15.

Material LG-75 is that which contains the least cross-linking agent. Its reaction field, appears to be composed of two exotherms.

The increase in the content of cross-linking agent with formulation LG-76 leads to an increase in the total enthalpy of cross-linking. In other words, substitution of the α,ω-bis(azide) oligomers with the cross-linking agent induces a greater heat release. The high-temperature shoulder shifts towards the higher temperatures, revealing a difference in reactivity between the two azide-containing molecules (cross-linking agent and α,ω-bis(azide) oligomer) with respect to the α,ω-bis(propargyl) oligomer.

The same tendencies are exacerbated with the mixture highest in cross-linking agent (i.e., formulation LG-78).

It is important to note that, despite the difference in reactivity of the azide-containing molecules (cross-linking agent and α,ω-bis(azide) oligomer), the cross-linking reaction is quantitative. Thus, preparation of the mixture in stoichiometric amounts (i.e., in the cross-linkable compositions leading to materials LG-75, LG-76, LG-77 and LG-78, the respective molar proportions of oligomers (i), (ii) and (iii) are such that the total number of propargyl (—CH$_2$—C≡CH) groups is equal to the total number of azide (—N$_3$) groups) ensures total consumption of the reactive species.

The lowest $T_g$ of the order of −100° C., as for it, is observed with the formulation lowest in cross-linking agent, which is consistent with the fact that the network is produced by highly flexible perfluorinated links.

7.4. Ternary Formulations with Pentaerythritol Triazide and Oligomers A' and B' (Examples 3 and 4): Variation of the Proportion of Cross-Linking Agent C Six materials were prepared with variable ratios of α,ω-bis(azide) oligomers/cross-linking agent (here, pentaerythritol triazide C) in the starting cross-linkable composition (formulations F1 to F6 below):

| Percentage of azide functions | |
| --- | --- |
| name | provided by C |
| F1 | 100% |
| F2 | 80% |
| F3 | 60% |
| F4 | 40% |
| F5 | 20% |
| F6 | 7% |

Infrared spectroscopy analyses confirmed the disappearance of the bands characteristic of alkyne- and azide-type groups. The polymerization is thus quantitative. The increase in the content of cross-linking agent leads to an increase in the total enthalpy of cross-linking (measured by differential calorimetric analysis): H(F1)=188 J/g, H(F2)=185 J/g, H(F3)=172 J/g, H(F4)=148 J/g, H(F5)=141 J/g, H(F6)=137 J/g.

Kinetic rheological analyses at 120° C. make it possible to monitor the reaction of the three reactive species. In all cases, the formulations lead to thermosetting matrices. The gel time thereof (associated with the minimum duration necessary for critical formation of a percolating network) is evaluated by time corresponding to the divergence of the viscoelastic moduli. They are 0.8, 1.2, 1.8, 3.5, 8.25 and 16 hours for formulations F1, F2, F3, F4, F5 and F6, respectively. In other words, gel time increases when the proportion of cross-linking agent decreases in the reaction formulation. At the same time, mechanical stiffness also decreases with the decreasing content of cross-linking agent.

Calorimetric analyses carried out on the formulations after total consumption of the reactive species show the presence of two glass-transition temperatures. The one recorded at low temperature is inherent to the (macro) molecular PFPE segments given by A' and/or B'. It is considered the secondary $T_g$ and remains constant (independent of the content of cross-linking agent) at about −103° C. The one observed at higher temperature, considered the principal $T_g$ of the polymer network, decreases with a decreasing proportion of cross-linking agent due to a larger, more flexible polymer mesh. It ranges from about −25° C. for formulation F1, to about −85° C. for formulation F6.

Finally, thermogravimetric analyses carried out under oxidizing atmosphere confirmed the formation of material having high thermal stability, with a decomposition temperature at 10% weight loss ($T_d^{10\%}$) higher than 300° C. for the six compositions F1 to F6.

Example 8: Polymerization with a Phosphorus-Containing Cross-Linking Agent

The enthalpy of cross-linking of an A+C binary mixture is determined by DSC, using the "Proteus Analysis" software. It is of the same order of magnitude as that of an A+C mixture containing 10% molar C' (see FIG. 24). The presence of the phosphorus group is thus not in itself an element that disrupts the overall reactivity of the mixture.

The invention claimed is:
1. A cross-linkable composition, comprising:
 i) a fluorinated α,ω-bis(propargyl) oligomer of formula (I):

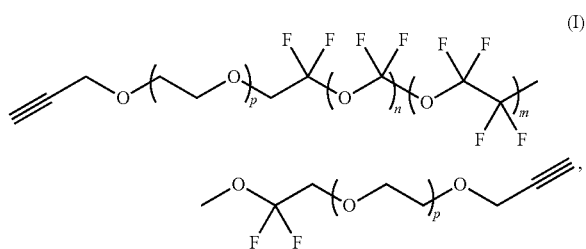

wherein
m is 1 to 100,
n is 2 to 150, and
p is 0 to 2,
n, m and p being selected such that the fluorinated α,ω-bis(propargyl) oligomer of formula (I) has a number-average molar mass ($M_n$) of 400 to 25000 as measured by $^{19}$F NMR spectroscopy;

ii) a cross-linking agent of formula (III):

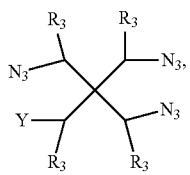

(III)

wherein
$R_3$ is a hydrogen atom, a $C_1$-$C_6$ aliphatic group, or an aromatic group,
Y is a group selected from H, OH, an aromatic group, a $C_1$-$C_6$ aliphatic group, or an $O(CH_2)_sP(O)(OR_4)_2$ group,
s an integer from 2 to 20,
$R_4$ being H or a $C_1$-$C_6$ aliphatic group; and
iii) optionally, a fluorinated oligomer comprising two terminal azide (—$N_3$) groups.

2. The cross-linkable composition according to claim 1, wherein respective molar proportions of oligomers (i) and (iii) and of cross-linking agent (ii) are such that a total number of propargyl (—$CH_2$—C≡CH) groups is equal to a total number of azide (—$N_3$) groups.

3. The cross-linkable composition according to claim 1, wherein Y is OH, $OCH_2CH_2P(O)(OH)_2$ or $OCH_2CH_2P(O)(OCH_3)_2$.

4. The cross-linkable composition according to claim 1, wherein the fluorinated α,ω-bis(azide) oligomer is represented by the following formula (IV):

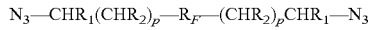

(IV), wherein:
radical $R_F$ is a fluorinated chain,
p is 0 or 1, and
$R_1$ and $R_2$ are independently selected from a hydrogen atom, a $C_1$-$C_6$ alkyl and a $C_2$-$C_6$ alkenyl.

5. The cross-linkable composition according to claim 4, wherein the fluorinated α,ω-bis(azide) oligomer is represented by the formula (V):

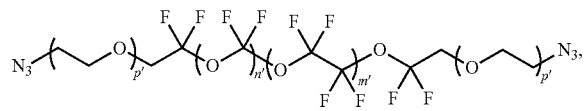

(V)

wherein:
m' is 1 to 100,
n' is 2 to 150, and
p' is 0 to 2, n', m' and p' being selected such that the fluorinated α,ω-bis(propargyl) oligomer of formula (I) has a number-average molar mass ($M_n$) of 400 to 25000; or the fluorinated α,ω-bis(azide) oligomer is represented by the formula (VI):

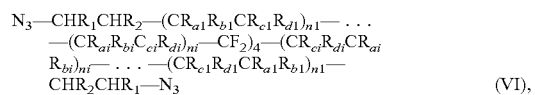

(VI), wherein:
$R_1$ and $R_2$ are independently selected from a hydrogen atom, a $C_1$-$C_6$ alkyl and a $C_2$-$C_6$ alkenyl,
i is 1 to 20,
$CR_{a1}R_{b1}CR_{c1}R_{d1}$ to $CR_{ai}R_{bi}CR_{ci}R_{di}$ are constitutional moieties, which may be identical or different, derived from monomers independently selected from the following fluorinated olefins: tetrafluoroethylene; vinylidene fluoride; hexafluoropropylene; trifluoroethylene; perfluoro(methyl vinyl ether); 3,3,3-trifluoropropene; 2,3,3,3-tetrafluoropropene; 1,3,3,3-tetrafluoropropene; chlorotrifluoroethylene; bromotrifluoroethylene; iodotrifluoroethylene; 2-chloro-3,3,3-trifluoropropene; vinyl fluoride; perfluoro(ethyl vinyl ether); perfluoro(propyl vinyl ether); 2-bromo-1,1-difluoroethylene; chlorodifluoroethylene; dichlorodifluoroethylene; 1,1,3,3,3-pentafluoropropene; 1,1,2,3,4,4-hexafluoro-1,3-butadiene; 1-propene, 1,1,3,3,3-pentafluoro-2-(trifluoromethyl)-1-propene; and derivatives thereof, and
$n_1$ to $n_i$ are each independently a number selected from 1 to 20.

6. The composition according to claim 1, wherein p is 1.75.

7. A material, comprising a product of a click-chemistry reaction of the cross-linkable composition according to claim 1 and having at least one glass-transition temperature value of −70° C. or lower.

8. The material according to claim 7, wherein the material has a decomposition temperature at 10% weight loss ($T_d^{10\%}$) of 250° C. or higher, in air.

9. The material according to claim 7, wherein the material has at least one glass-transition temperature value of −80° C. or lower.

10. A process for preparing the material according to claim 7, the process comprising performing a cross-linking by click chemistry between:
i) a fluorinated α,ω-bis(propargyl) oligomer of formula (I):

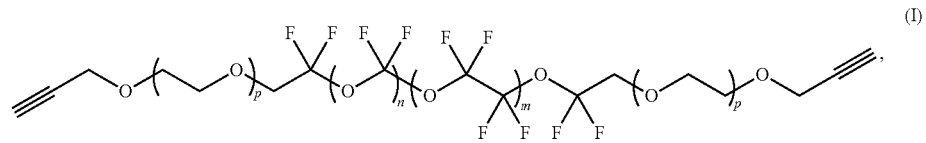

(I)

wherein:
m is 1 to 100,
n is 2 to 150, and
p is 0 to 2, n, m and p being selected such that the fluorinated α,ω-bis(propargyl) oligomer of formula (I) has a number-average molar mass ($M_n$) of 400 to 25000 as measured by $^{19}$F NMR spectroscopy;

ii) a cross-linking agent of formula (III):

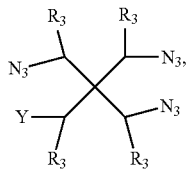

(III)

wherein:

$R_3$ is a hydrogen atom, a $C_1$-$C_6$ aliphatic group, or an aromatic group, and Y is a group selected from H, OH, an aromatic group, a $C_1$-$C_6$ aliphatic group, an $O(CH_2)_sP(O)(OR_4)_2$ group, s an integer from 2 to 20, $R_4$ being H or a $C_1$-$C_6$ aliphatic group, notably a methyl, ethyl or isopropyl group; and iii) optionally, a fluorinated oligomer comprising two terminal azide (—$N_3$) groups.

11. The process according to claim 10, wherein the cross-linking occurs in the presence of a copper catalyst.

12. An electrical insulator, comprising the material of claim 7.

13. The electrical insulator according to claim 12, which is suitable as an encapsulant for electronic cards in on-board systems or power modules, coatings for rotary machines or electric motors, semi-rigid packaging components, wiring.

14. The electrical insulator according to claim 12, wherein the material has a decomposition temperature at 10% weight loss ($T_d^{10\%}$) of 250° C. or higher, in air.

* * * * *